(12) United States Patent
Li et al.

(10) Patent No.: US 7,332,495 B2
(45) Date of Patent: Feb. 19, 2008

(54) ARALKYL-KETONE PIPERAZINE DERIVATIVES AND THEIR USES AS NEW ANTALGIC OR ATARACTIC AGENT

(75) Inventors: Jianqi Li, Shanghai (CN); Liying Huang, Shanghai (CN); Chunnian Zhang, Shanghai (CN); Xican Tang, Shanghai (CN); Guoyuan Hu, Shanghai (CN)

(73) Assignees: Nhwa Pharma. Corporation, Jiangsu (CN); Shanghai Institute of Pharmaceutical Industry, Shanghai (CN)

( * ) Notice: Subject to any disclaimer, the term of this patent is extended or adjusted under 35 U.S.C. 154(b) by 460 days.

(21) Appl. No.: 10/515,308

(22) PCT Filed: Apr. 16, 2003

(86) PCT No.: PCT/CN03/00274

§ 371 (c)(1),
(2), (4) Date: Nov. 22, 2004

(87) PCT Pub. No.: WO03/097623

PCT Pub. Date: Nov. 27, 2003

(65) Prior Publication Data

US 2006/0148811 A1    Jul. 6, 2006

(30) Foreign Application Priority Data

May 22, 2002    (CN)    ................. 02 1 11786

(51) Int. Cl.
*A61K 31/497*    (2006.01)
*A61K 31/4965*    (2006.01)
*C07D 241/02*    (2006.01)
*C07D 401/00*    (2006.01)
*C07D 403/00*    (2006.01)
*C07D 405/00*    (2006.01)

(52) U.S. Cl. ............................ 514/252.13; 514/255.01; 514/255.05; 544/358; 544/377; 544/363; 544/360; 544/364

(58) Field of Classification Search .................... None
See application file for complete search history.

(56) References Cited

FOREIGN PATENT DOCUMENTS

| EP | A 370381 | 5/1990 |
|----|----------|--------|
| EP | A 558245 | 9/1993 |
| EP | A 558245 | 4/1995 |
| WO | WO 01/07431 | * 1/2001 |

\* cited by examiner

*Primary Examiner*—James O. Wilson
*Assistant Examiner*—Erich Leeser
(74) *Attorney, Agent, or Firm*—Crowell & Moring LLP

(57) ABSTRACT

Arylalkyl ketone piperazine derivatives of the formula:

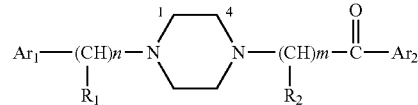

and pharmaceutical compositions comprising the same. Also disclosed are methods for using the compounds as analgesic and sedative agents. The compounds of the present invention have good analgesic and sedative activities but few side effects.

11 Claims, No Drawings

ARALKYL-KETONE PIPERAZINE DERIVATIVES AND THEIR USES AS NEW ANTALGIC OR ATARACTIC AGENT

FIELD OF INVENTION

The present invention relates to arylalkyl ketone piperazine derivatives and their applications as novel analgesic and sedative agents.

TECHNICAL BACKGROUND

Countless patients are suffering from severe acute or chronic pain, including pains associated with cancer and surgical operations. Pain treatment remains a serious clinical challenge. The current analgesic opioid drugs have side affects such as drug addiction, respiration restraint, stomach peristalsis reduction etc. Therefore, their clinical use is limited. There has always been a great need for novel centrally-acting analgesics having potent analgesic activities and clinical safety without the above side effects.

DESCRIPTION OF THE INVENTION

The first aspect of the present invention provides a series of arylalkyl ketone piperazine derivatives which are medically valuable. The aim is to overcome the defects of some current analgesic opioid drugs, such as drug addiction, respiration restraint, stomach peristalsis reduction, so as to satisfy the clinical needs for analgesics.

The second aspect of the present invention provides the application of the compounds above as novel antalgic and sedative agents.

The Arylalkyl ketone piperazine derivatives described in the present invention are free bases or salts of the compounds represented by the general formula below:

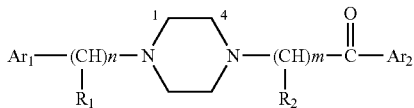

The salts are one of hydrochloride, hydrobromide, sulfate, trifluoroacetate or methanesulfonate etc., preferably hydrochloride or hydrobromide. It can contain about 0.5-3 molecules of hydrate water.

Wherein $Ar_1$ and $Ar_2$ independently represent:

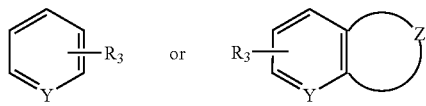

$R_1$, $R_2$ and $R_3$, each of them can represent any one of hydrogen, a $C_1$-$C_3$ alkyl group, a $C_5$ or $C_6$ cycloalkyl group, phenyl, substituted phenyl, hydroxyl, methoxy, ethoxy, amino, substituted amino, halogen, carboxylic acid, carboxylic ester, nitryl or acetonitrile group.

$R_1$, $R_2$ and $R_3$ represent preferably one of hydrogen, a $C_1$-$C_3$ alkyl group, hydroxyl, methoxy, ethoxy, amino, substituted amino, halogen or nitryl.

Y represents one of C, N, or O.

Z represents a five or six-member ring containing at least one of C, S, N or O.

n and m are independently 0, 1, 2 or 3.

The preferable compounds are included as follows:

IV-1 $N^1$-benzyl-$N^4$-phenacyl piperazine,
IV-2 $N^1$-(4-chlorobenzyl)-$N^4$-(1-benzoylethyl)piperazine,
IV-3 $N^1$-(4-chlorobenzyl)-$N^4$-phenacyl piperazine,
IV-4 $N^1$-(4-nitrobenzyl)-$N^4$-phenacyl piperazine
IV-5 $N^1$-[(1-ethoxy-oxo-methyl)benzyl]-$N^4$-phenacyl piperazine
IV-6 $N^1$-benzyl-$N^4$-(4-chlorophenacyl)piperazine
IV-7 $N^1$-benzyl-$N^4$-(2-naphthoylmethyl)piperazine
IV-8 $N^1$-benzyl-$N^4$-(4-methoxyphenacyl)piperazine
IV-9 $N^1$-benzyl-$N^4$-(4-nitrophenacyl)piperazine
IV-10 $N^1$-(4-methoxybenzyl)-$N^4$-phenacyl piperazine
IV-11 $N^1$-(3-pyridylmethyl)-$N^4$-phenacyl piperazine
IV-12 $N^1$-(4-aminobenzyl)-$N^4$-phenacyl piperazine
IV-13 $N^1$-(4-aminobenzyl)-$N^4$-(1-benzoylethyl)piperazine
IV-14 $N^1$-phenethyl-$N^4$-phenacyl piperazine
IV-15 $N^1$-(2,5-dimethoxybenzyl)-$N^4$-phenacyl piperazine
IV-16 $N^1$-benzyl-$N^4$-(4-aminophenacyl)piperazine
IV-17 $N^1$-benzyl-$N^4$-(2-benzoylethyl)piperazine
IV-18 $N^1$-(4-nitrobenzyl)-$N^4$-[(4-acetamido)phenacyl]piperazine
IV-19 $N^1$-(3,4-methylenedioxybenzyl)-$N^4$-phenacyl piperazine
IV-20 $N^1$-(4-fluorobenzyl)-$N^4$-(4-chlorophenacyl)piperazine
IV-21 $N^1$-(4-acetamidobenzyl)-$N^4$-phenacyl piperazine
IV-22 $N^1$-(3-phenylpropyl-3-ol)-$N^4$-(4-methoxyphenacyl)piperazine
IV-23 $N^1$-(2-methoxy-5-nitrobenzyl)-$N^4$-phenacyl piperazine
IV-24 $N^1$-[1-(4-fluorophenyl)ethyl]-$N^4$-phenacyl piperazine
IV-25 $N^1$-(3-methoxybenzyl)-$N^4$-phenacyl piperazine
IV-26 $N^1$-[(2-benzenesulfonylmethyl)benzyl]-$N^4$-phenacyl piperazine
IV-27 $N^1$-[1-(4-nitrophenyl)ethyl]-$N^4$-(4-methylphenacyl)piperazine
IV-28 $N^1$-benzyl-$N^4$-(5-chloro-6-methoxy-2-naphthoylmethyl)piperazine
IV-29 $N^1$-benzyl-$N^4$-[1-(5-chloro-6-methoxy-2-naphthoyl)ethyl]piperazine
IV-30 $N^1$-(3,4-methylenedioxybenzyl)-$N^4$-[1-(5-chloro-6-methoxy-2-naphthoyl)ethyl]piperazine
IV-31 $N^1$-(4-methoxybenzyl)-$N^4$-[1-(5-chloro-6-methoxy-2-naphthoyl)ethyl]piperazine
IV-32 $N^1$-(4-nitrobenzyl)-$N^4$-[1-(5-chloro-6-methoxy-2-naphthoyl)ethyl]piperazine
IV-33 $N^1$-(4-aminobenzyl)-$N^4$-[1-(5-chloro-6-methoxy-2-naphthoyl)ethyl]piperazine
IV-34 $N^1$-(3,4,5-trimethoxybenzyl)-$N^4$-[1-(5-chloro-6-methoxy-2-naphthoyl)ethyl]piperazine
IV-35 $N^1$-cinnamyl $N^4$-[1-(5-chloro-6-methoxy-2-naphthoyl)ethyl]piperazine
IV-36 $N^1$-(3-chlorobenzyl)-$N^4$-[1-(5-chloro-6-methoxy-2-naphthoyl)ethyl]piperazine
IV-37 $N^1$-(1-phenylethyl)-$N^4$-phenacyl piperazine
IV-38 $N^1$—(R-1-phenylethyl)-$N^4$-phenacyl piperazine
IV-39 $N^1$-(S-1-phenylethyl)-$N^4$-phenacyl piperazine
IV-40 $N^1$-(1-phenylethyl)-$N^4$-(4-methylphenacyl)piperazine
IV-41 $N^1$—(R-1-phenylethyl)-$N^4$-(4-methylphenacyl)piperazine
IV-42 $N^1$-(S-1-phenylethyl)-$N^4$-(4-methylphenacyl)piperazine
IV-43 $N^1$-(1-phenylethyl)-$N^4$-[1-(5-chloro-6-methoxy-2-naphthoyl)ethyl]piperazine IV-44 N¹-(S-1-phenylethyl)-N⁴-[1-(5-chloro-6-methoxy-2-naphthoyl)ethyl]piperazine
IV-45 N¹—(R-1-phenylethyl)-N⁴-[1-(5-chloro-6-methoxy-2-naphthoyl)ethyl]piperazine
IV-46 N¹-(4-chlorobenzyl)-N⁴-phenacyl piperazine
IV-47 N¹-(4-nitrobenzyl)-N⁴-(1-benzoylethyl)piperazine
IV-48 N¹-(1-phenylethyl)-N⁴-(1-benzoylethyl)piperazine
IV-49 N¹-(2,4-dichlorobenzyl)-N⁴-phenacyl piperazine
IV-50 N¹-(4-chlorobenzyl)-N⁴-(4-chlorophenacyl)piperazine
IV-51 N¹-[(1-hydroxy-oxo-methyl)benzyl]-N⁴-phenacyl piperazine
IV-52 N¹-[(1-ethoxy-oxo-methyl)benzyl]-N⁴-(1-benzoylethyl)piperazine
IV-53 N¹-(4-fluorobenzyl)-N⁴-phenacyl piperazine
IV-54 N¹-benzyl-N⁴-[2-(benzylamino)-2-oxo-ethyl]piperazine
IV-55 N¹-benzyl-N⁴-(4-acetamido phenacyl)piperazine
IV-56 N¹-benzyl-N⁴-[1-oxo-2-(4-phenylpiperazin-1-yl)ethyl]piperazine
IV-57 N¹-benzyl-N⁴-(1-benzoylbenzyl)piperazine
IV-58 N¹-(1-naphthalenylmethyl)-N⁴-phenacyl piperazine
IV-59 N¹-(2-naphthalenylmethyl)-N⁴-phenacyl piperazine
IV-60 N¹-[1-(4-nitrophenyl)ethyl]-N⁴-phenacyl piperazine
IV-61 N¹-(1-phenylpropyl)-N⁴-phenacyl piperazine
IV-62 N¹-(4-nitrobenzyl)-N⁴-[2-(benzylamino)-2-oxo-ethyl]piperazine
IV-63 N¹-(4-benzyloxybenzyl)-N⁴-phenacyl piperazine, and
IV-64 N¹-(4-aminobenzyl)-N⁴-[2-(benzylamino)-2-oxo-ethyl]piperazine A particularly preferable compound is IV-12 N¹-(4-aminobenzyl)-N⁴-phenacyl piperazine Their structures are shown in Table 1.

TABLE 1

| NO. | Ar₁ | Ar₂ | R₁ | R₂ | n | m |
|---|---|---|---|---|---|---|
| IV-1 | Ph | Ph | H | H | 1 | 1 |
| IV-2 | Cl—C₆H₄— (4-Cl-phenyl) | Ph | H | CH₃ | 1 | 1 |
| IV-3 | Cl—C₆H₄— (4-Cl-phenyl) | Ph | H | H | 1 | 1 |
| IV-4 | O₂N—C₆H₄— (4-NO₂-phenyl) | Ph | H | H | 1 | 1 |
| IV-5 | Ph | Ph | COOC₂H₅ | H | 1 | 1 |
| IV-6 | Ph | Cl—C₆H₄— (4-Cl-phenyl) | H | H | 1 | 1 |
| IV-7 | Ph | naphthyl | H | H | 1 | 1 |
| IV-8 | Ph | CH₃O—C₆H₄— (4-MeO-phenyl) | H | H | 1 | 1 |
| IV-9 | Ph | O₂N—C₆H₄— (4-NO₂-phenyl) | H | H | 1 | 1 |
| IV-10 | CH₃O—C₆H₄— (4-MeO-phenyl) | Ph | H | H | 1 | 1 |
| IV-11 | 3-pyridyl | Ph | H | H | 1 | 1 |
| IV-12 | H₂N—C₆H₄— (4-NH₂-phenyl) | Ph | H | H | 1 | 1 |

TABLE 1-continued

| NO. | Ar₁ | Ar₂ | R₁ | R₂ | n | m |
|---|---|---|---|---|---|---|
| IV-13 | H₃N–C₆H₄– | Ph | H | CH₃ | 1 | 1 |
| IV-14 | Ph | Ph | H | H | 2 | 1 |
| IV-15 | 2,4-(CH₃O)₂-C₆H₃– | Ph | H | H | 1 | 1 |
| IV-16 | Ph | H₂N–C₆H₄– | H | H | 1 | 1 |
| IV-17 | Ph | Ph | H | H | 1 | 2 |
| IV-18 | 4-NO₂–C₆H₄– | 4-NHCOCH₃–C₆H₄– | H | H | 1 | 1 |
| IV-19 | 3,4-methylenedioxyphenyl | Ph | H | H | 1 | 1 |
| IV-20 | 4-F–C₆H₄– | 4-Cl–C₆H₄– | H | H | 1 | 1 |
| IV-21 | 4-NHCOCH₃–C₆H₄– | Ph | H | H | 1 | 1 |
| IV-22 | Ph-CH(OH)- | 4-CH₃O–C₆H₄– | H | H | 2 | 1 |
| IV-23 | 3-NO₂-4-OCH₃–C₆H₃– | Ph | H | H | 1 | 1 |
| IV-24 | 4-F–C₆H₄– | Ph | CH₃ | H | 1 | 1 |
| IV-25 | 3-CH₃O–C₆H₄– | Ph | H | H | 1 | 1 |
| IV-26 | 2-(PhSO₂CH₂)–C₆H₄– | Ph | H | H | 1 | 1 |
| IV-27 | 4-NO₂–C₆H₄– | 4-CH₃–C₆H₄– | CH₃ | H | 1 | 1 |

TABLE 1-continued
| NO. | Ar₁ | Ar₂ | R₁ | R₂ | n | m |
|---|---|---|---|---|---|---|
| IV-28 | Ph | 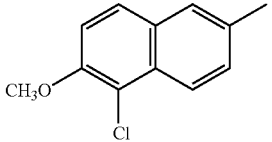 | H | H | 1 | 1 |
| IV-29 | Ph | 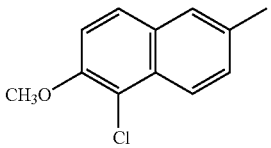 | H | CH₃ | 1 | 1 |
| IV-30 | 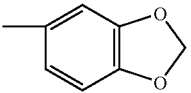 | 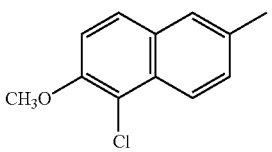 | H | CH₃ | 1 | 1 |
| IV-31 | 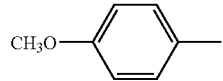 | 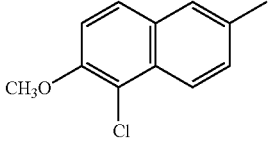 | H | CH₃ | 1 | 1 |
| IV-32 | 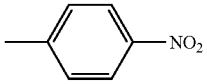 | 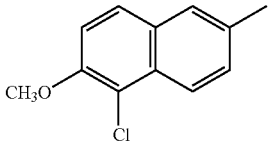 | H | CH₃ | 1 | 1 |
| IV-33 | 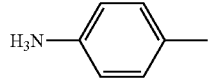 | 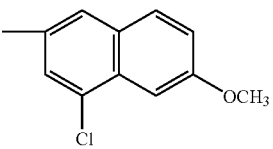 | H | CH₃ | 1 | 1 |
| IV-34 | 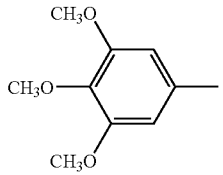 | 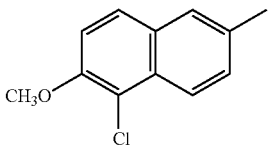 | H | CH₃ | 1 | 1 |
| IV-35 | 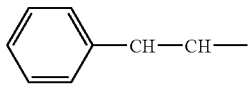 | 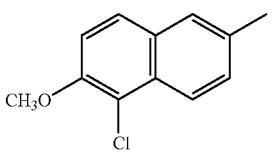 | H | CH₃ | 1 | 1 |
| IV-36 | 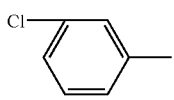 | 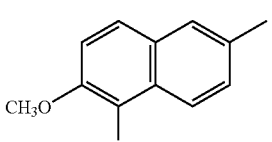 | 0 | CH₃ | 0 | 1 |
| IV-37* | Ph | Ph | CH₃ | H | 1 | 1 |

TABLE 1-continued

| NO. | Ar₁ | Ar₂ | R₁ | R₂ | n | m |
|---|---|---|---|---|---|---|
| IV-40* | Ph | 4-CH₃-C₆H₄- | CH₃ | H | 1 | 1 |
| IV-43* | Ph | 1-Cl-2-CH₃O-6-CH₃-naphthyl | CH₃ | CH₃ | 1 | 1 |
| IV-46 | Ph | Ph | H | CH₃ | 1 | 1 |
| IV-47 | 4-NO₂-C₆H₄- | Ph | H | CH₃ | 1 | 1 |
| IV-48 | Ph | Ph | CH₃ | CH₃ | 1 | 1 |
| IV-49 | 2,5-Cl₂-C₆H₃- | Ph | H | H | 1 | 1 |
| IV-50 | 4-Cl-C₆H₄- | 4-Cl-C₆H₄- | H | H | 1 | 1 |
| IV-51 | Ph | Ph | COOH | H | 1 | 1 |
| IV-52 | Ph | Ph | COOC₂H₅ | CH₃ | 1 | 1 |
| IV-53 | 4-F-C₆H₄- | Ph | H | H | 1 | 1 |
| IV-54 | Ph | —NH—C₆H₅ | H | H | 1 | 1 |
| IV-55 | Ph | 4-NHCOCH₃-C₆H₄- | H | H | 1 | 1 |
| IV-56 | Ph | —CH₂N(piperazine)NCH₂Ph | H | 0 | 1 | 0 |
| IV-57 | Ph | Ph | H | Ph | 1 | 1 |
| IV-58 | 1-naphthyl | Ph | H | H | 1 | 1 |
| IV-59 | 2-naphthyl | Ph | H | H | 1 | 1 |
| IV-60 | 4-NO₂-C₆H₄- | Ph | CH₃ | H | 1 | 1 |
| IV-61 | Ph | Ph | CH₂CH₃ | H | 1 | 1 |

TABLE 1-continued

| NO. | Ar₁ | Ar₂ | R₁ | R₂ | n | m |
|---|---|---|---|---|---|---|
| IV-62 | 4-NO₂-C₆H₄- | —NHCH₂-C₆H₅ | H | H | 1 | 1 |
| IV-63 | C₆H₅-CH₃O-C₆H₄- | Ph | H | H | 1 | 1 |
| IV-64 | 4-NH₂-C₆H₄- | —NHCH₂-C₆H₅ | H | H | 1 | 1 |

*a racemic compound and its corresponding optical isomers

Compounds according to the present invention can be prepared as follows:

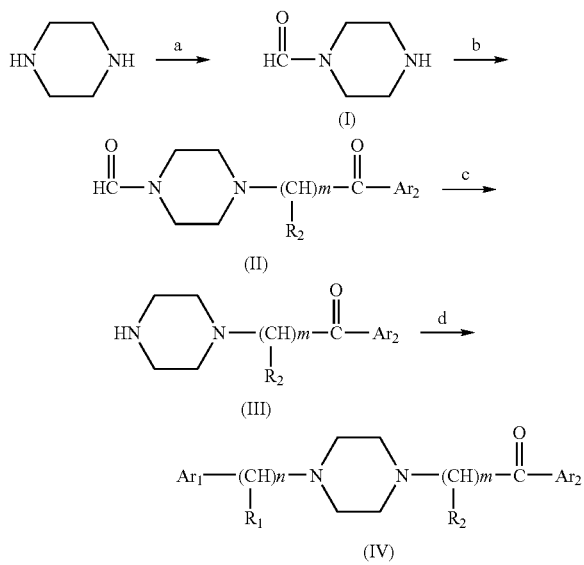

a: HCOOCH₃;

b: Ar₂C(CH)ₘX; K₂CO₃, KI, CH₃COOCH₃ c: 2N NaOH;

d: Ar₁(CH)ₙX; K₂CO₃, KI, DMSO
    |
    R₁

Piperazine is used as a starting material to prepare the above-mentioned compounds. One of the N atoms of the piperazine ring is protected by a formyl group first, and then alkylated, finally the formyl group is removed by alkaline hydrolysis to obtain compound (III) with a higher purity and yield. The total yield of three procedures is about 40%. Compound (III), an important intermediate, is alkylated at $N^4$ with corresponding halide to obtain the goal compound (IV). When using K₂CO₃/DMF, the reaction can take place at room temperature, and the yield is about 80%. If using K₂CO₃/CH₃COCH₃, NaHCO₃/C₂H₅OH, or Et₃N/CHCl₃ as reaction systems, the reaction needs to be refluxed for 8-24 h, and the color of the reaction will become deeper and deeper as time passes. This will reduce the quality and yield of the products. The goal compounds IV-1 to IV-64 are obtained by the above-mentioned procedures.

Halogenated aralkyl formyl alkyl compounds in step b and d can be provided commercially and also be prepared by using bromine or copper bromide with corresponding aralkyl ketones.

The coupounds described in this invention can be used as analgesic or sedative agents.

Most compounds described in this invention have potent analgesic effects when tested using chemical writhing model in mice. Results obtained with four models of two animal species showed that compound IV-12 has a greater therapeutic index and a greater oral absorption than the rest. Its antalgic activity is comparable to morphine, but much better than Paracetamol. IV-12 has no apparent affinity with the morphine μ receptor, suggesting that it is a new kind of non-opioid analgesic compound; IV-12 showed obvious central antalgic effects without antifebrile or anti-inflammatory activities. Various experiments in rats and mice indicate that IV-12 has no physical addiction, and psychological dependence is weak. Its Ames test is negative. All of the results show that the IV-12 has a potential value as a noval non-addictive analgesic agent.

Compounds described in this invention are used as pharmaceutical compositions for patients in need thereof orally or via injection and so on.

The pharmaceutical compositions mentioned above comprise an effective amount of the compounds in this invention with at least one of many pharmaceutically acceptable carriers.

The carriers mentioned above represent the routine pharmaceutical carriers, such as dilutents, excipients (water, etc), adhesives (fibrin derivatives, gelatin, polyvinyl, pyrrolidone, etc), filling materials (starch, etc), disitegrants (calcium carbonate, sodium bicarbonate, etc) lubricants (calcium stearate, magnesium stearate, etc) and other auxiliary materials such as flavor and edulcorant.

For oral administration, the compounds can be prepared into regular solid formulations, such as tablets, powders or capsules. For injection, it can be prepared into liquid form.

Each formulation of the compositions in this invention can be prepared by conventional pharmaceutical methods, and the content of the active compound is about 0.1-99.5%.

The inventors also discovered that the inventive compounds have low toxicity and few side effects on the central nervous system.

EXAMPLES

General Preparation 1: N-aralkyl formylalkyl piperazine dihydrochloride (III)

A mixture of anhydrous piperazine (258 g, 3 mol) and methyl formate (180 g, 3 mol) was refluxed for 8 h, excessive unreacted piperazine was removed in vacuo, 240 g of N-formyl piperazine (70%) was obtained, via distilling at 130-134° C./8-10 mmHg.

A mixture of the above product (310 mmol), aralkyl formylalkyl halogen (372 mmol), $K_2CO_3$ (465 mmol) and KI (30 mmol) in 320 ml of acetone was refluxed for 8-16 h, filtered off; the filtrate was evaporated in vacuo. 5% NaOH (350 ml) was added to the residue. The reaction is refluxed for 10 h, and its pH is adjusted to 8 with 6N HCl, followed by an extraction with $CHCl_3$ (200 ml×3). The combined organic layer was washed once each with 50 ml of water and saturated NaCl solution, dried with $mgSO_4$, filtered and remaining solvent evaporated. The residue was dissolved in 20 ml of ethanol, and then adjusted to a pH of 3 with $HCl/C_2H_5OH$ (5N), the resulting precipitate was recrystallized with anhydrous ethanol to obtain N-aralkyl formylalkyl piperazine dihydrochloride (III) (55-60%).

General Preparation 2: $N^1$-aralkylformylalkyl-$N^4$-aralkyl piperazine dihydrochloride A mixture of compound III (10 mmol), aralkyl halogen (12 mmol), KI (1 mmol) and $K_2CO_3$ (35 mmol) in 50 ml of DMF or anhydrous acetone was stirred at 25° C.-60° C. for 8-12 h, filtrated, and then evaporated to dryness. The residue is dissolved in 50 ml of water, and extracted with EtOAc (100 ml×3). The organic phase was combined, washed with $H_2O$ and saturated with NaCl, dried ($mgSO_4$). Filtered and evaporated, the residue was dissolved by 30 ml of ethanol and then adjusted to a PH of 2 by $HCl/C_2H_5OH$ (5N); the resulting precipitate was recrystallized from ethanol or $CH_3OH$ to obtain the title compound (IV) (60-85%).

Example 1

IV-1 $N^1$-benzyl-$N^4$-phenacyl piperazine dihydrochloride

A mixture of N-benzyl piperazine dihydrochloride (3.98 g, 16 mmol), 2-chloro-1-phenylethanone (2.97 g, 19.2 mmol) and anhydrous $K_2CO_3$ (7.73 g, 56 mmol) in 180 ml of acetone was treated according to the general preparation 2 to give 4.5 g of compound (IV-1), yield (75%), mp 238-9° C. $M^+$ 294.

Elementary alanalysis: $C_{19}H_{22}N_2O.2HCl.H_2O$. Found: (% C, 59.38; H, 6.51; N, 7.12; Cl, 18.23); theoretical value (% C, 59.31; H, 6.8; N, 7.27; Cl, 18.4). IR (KCl): ν 2950, 1710, 1600, 1500 $cm^{-1}$. $^1HNMR$ (DMSO-$d_6$): δ 3.58 (m, 8H, piperazine-H), 4.50 (s, 2H, $PhCH_2$), 5.22 (s, 2H, $COCH_2N$), 7.40-8.10 (m, 10H, ArH).

Example 2

IV-2 $N^1$-(4-chlorobenzyl)-$N^4$-(1-benzoylethyl)piperazine dihydrochloride

A mixture of N-(4-chlorobenzyl)piperazine dihydrochloride (5 g, 20 mmol), anhydrous $KHCO_3$ (70 mmol) and 2-bromo-1-phenylpropan-1-one (3.96 ml, 26 mmol) in 40 ml of anhydrous ethanol was refluxed for 8 hours, and then treated according to general preparation 2 to give 6.1 g of compound (IV-2), yield 59.51%, mp 260-262° C. $M^+$ 342.

Elementary analysis: $C_{20}H_{23}ClN_2O.2HCl.H_2$. Actual: (% C, 55.01; H, 6.01; N, 6.41; theoretical value (% C, 55.37; H, 6.27; N, 6.46).

Example 3

IV-3 $N^1$-(4-chlorobenzyl)-$N^4$-phenacyl piperazine dihydrochloride

A mixture of N-(4-chlorobenzyl)piperazine dihydrochloride (5 g, 20 mmol), triethylamine (5.58 ml, 40 mmol) and 2-chloro-1-phenylethanone (4.08 g, 26 mmol) in 40 ml of anhydrous ethanol was refluxed for 8 hours, and then treated according to general preparation 2 to give 5.2 g of compound (IV-3), yield 59.51%, mp 256-258° C. $M^+$ 328.

Elementary analysis: $C_{19}H_{21}ClN_2O.2HCl.H_2O$. Actual: (% C, 55.01; H, 6.01; N, 6.41); theoretical value (% C, 55.37; H, 6.27; N, 6.46).

Example 4

IV-4 $N^1$-(4-nitrobenzyl)-$N^4$-phenacyl piperazine dihydrochloride

A mixture of N-(4-nitrobenzyl)piperazine dihydrochloride (7.73 g, 30 mmol), triethylamine (8.37 ml, 60 mmol) and 2-chloro-1-phenylethanone (6.12 g, 39 mmol) in 100 ml of benzene was refluxed for 5 hours, and then treated according to general preparation 2 to give 5.2 g of compound (IV-4), yield 59.51%, mp 236-238° C. $M^+$ 339.

Elementary analysis: $C_{19}H_{21}N_3O_3.2HCl.H_2O$. Actual: (% C, 53.98; H, 5.53; N, 9.91); theoretical value (% C, 54.16; H, 5.74; N, 9.97).

Example 5

IV-5 $N^1$-[(1-ethoxy-oxo-methyl)benzyl]-$N^4$-phenacyl piperazine dihydrochloride A mixture of N-formyl piperazine 35.5 g (310 mmol), 2-chloro-1-phenylethanone (57.6 g, 372 mmol) and anhydrous $K_2CO_3$ (64.3 g, 465 mmol) in 320 ml of acetone was treated according to general preparation 1 to give 49 g of N-phenacyl piperazine dihydrochloride, yield 57%, mp 246-8° C. (dec). $M^+$ 204.

$^1HNMR$ (DMSO-d6): δ3.50 (m, 8H, piperazine-H), 5.20 (s, 2H, $COCH_2N$), 7.57-8.01 (m, 5H, ArH), 10.13 (br,1H, NH).

A mixture of the above compound (2 g, 7.2 mmol), ethyl 2-chloro-2-phenylacetate (1.72 g, 8.64 mmol) and $K_2CO_3$ (3.48 g, 25.2 mmol) in 40 ml of DMF was treated according to general preparation 2 to give compound (IV-5), yield 60%, mp 182° C. (dec). $M^+$ 366.

Elementary analysis: $C_{22}H_{26}N_2O_3.2HCl.H_2O$. Actual: (% C, 57.54; H, 5.90; N, 6.83); theoretical value (% C, 57.15; H, 6.00; N, 6.67).

Example 6

IV-6 $N^1$-benzyl-$N^4$-(4-chloro phenacyl)piperazine dihydrochloride

A mixture of N-benzyl piperazine dihydrochloride (2.49 g, 10 mmol), $K_2CO_3$ (4.14 g, 30 mmol) and 2-bromo-1-(4-chlorophenyl)ethanone (2.8 g, 12 mmol) in 100 ml of acetone was refluxed for 5 hours, and then treated according to general preparation 2 to give 2.76 g of compound (IV-6), yield 68.7%, mp 231-233° C. M+ 328.

Elementary analysis: $C_{19}H_{21}ClN_2O.2HCl$. Actual: (% C, 56.61; H, 5.73; N, 6.98); theoretical value (% C, 56.79; H, 5.73; N, 6.97).

Example 7

IV-7 $N^1$-benzyl-$N^4$-(2-naphthoylmethyl)piperazine dihydrochloride

A mixture of N-benzyl piperazine dihydrochloride (1.25 g, 5 mmol), 2-bromo-1-(naphthalen-2-yl)ethanone (1.50 g, 6 mmol) and $K_2CO_3$ (2.07 g, 15 mmol) in 80 ml of acetone was treated according to general preparation 2 to give 1.56 g of compound (IV-7) as white solid, yield 74.82%, mp 241° C. (dec). M+ 344.

Elementary analysis: $C_{23}H_{24}N_2O.2HCl.H_2O$. Actual: (% C, 66.58; H, 6.29; N, 6.57); theoretical value (% C, 66.19; H, 6.24; N, 6.71). IR (KCl): ν 2900, 1700, 1630, 1600 cm$^{-1}$. $^1$HNMR (DMSO-d6): δ3.57 (m, 8H, piperazine-H), 4.48 (s, 2H, PhCH$_2$), 5.33 (s, 2H, NCH$_2$CO), 7.46-8.14 (m, 12H, ArH).

Example 8

IV-8 $N^1$-benzyl-$N^4$-(4-methoxy phenacyl)piperazine dihydrochloride

A mixture of N-benzyl piperazine dihydrochloride (1.37 g, 5 mmol), 2-bromo-1-(4-methoxyphenyl)ethanone (1.50 g, 6 mmol, Aldrich) and $K_2CO_3$ (2.28 g, 16.5 mmol) in 80 ml of acetone was treated according to general preparation 2 to give 1.88 g compound as white solid (IV-8), yield 70%, mp 228-230° C. M+ 308.

Elementary analysis: $C_{20}H_{24}N_2O_2.2HCl.H_2O$. Actual: (% C, 55.12; H, 6.90; N, 6.34); theoretical value (% C, 55.43; H, 6.93; N, 6.47). IR (KCl): ν 2900, 1700, 1630, 1600 cm$^{-1}$.

Example 9

IV-9 $N^1$-benzyl-$N^4$-(4-nitro phenacyl)piperazine dihydrochloride

A mixture of N-phenacyl piperazine dihydrochloride (1.50 g, 6 mmol), 2-bromo-1-(4-nitrophenyl)ethanone (1.75 g, 7.2 mmol) and $K_2CO_3$ (2.48 g, 18 mmol) in 80 ml of acetone was treated according to general preparation 2 to give 1.18 g of compound (IV-9) as white solid, yield 70%, mp 236-238° C. M+ 339.

Elementary analysis: $C_{19}H_{21}N_3O_3.2HCl.1/2H_2O$. Actual: (% C, 54.23; H, 5.56; N, 9.90); theoretical value (% C, 54.16; H, 5.70; N, 9.98). IR (KCl): ν 2900, 1710, 1640, 1600 cm$^{-1}$.

Example 10

IV-10 $N^1$-(4-methoxybenzyl)-$N^4$-phenacyl piperazine dihydrochloride

A mixture of N-phenacyl piperazine dihydrochloride (1.40 g, 5.1 mmol), 4-methoxybenzyl chloride (1.36 g, 8.7 mmol) and $K_2CO_3$ (2.11 g, 15.3 mmol) in 80 ml of acetone was treated according to general preparation 2 to give 1.2 g of compound (IV-10) as white solid, yield 70%, mp 222-224° C. M+ 324.

Elementary analysis: $C_{20}H_{24}N_2O_2.2HCl.1/2H_2O$. Actual: (% C, 59.47; H, 6.78; N, 7.19); theoretical value (% C, 59.12; H, 6.70; N, 6.89). IR (KCl): ν 2900, 1710, 1640, 1600 cm$^{-1}$.

Example 11

IV-11 $N^1$-(3-pyridylmethyl)-$N^4$-phenacyl piperazine trihydrochloride

A mixture of N-phenacyl piperazine dihydrochloride (1 g, 3.6 mmol), 3-(chloromethyl)pyridine (0.71 g, 4.3 mmol) and anhydrous $K_2CO_3$ (2.2 g, 16 mmol) in 15 ml of DMF was treated according to general preparation 2, and then recrystallized with ethnol to give 1 g of compound (IV-11), yield 65.79%, mp 225-6° C. M+ 295.

Elementary analysis: $C_{18}H_{21}N_3O.3HCl.H_2O$. Actual: (% C, 50.75; H, 6.16; N, 10.14); theoretical value (% C, 51.17; H, 6.20; N, 9.95). IR: (KCl) ν 3400, 2890, 1690, 1630, 1590 cm$^{-1}$ $^1$HNMR (DMSO-d6): δ 3.33-3.54 (m, 8H, piperazine-H), 4.33 (s, 2H, CH$_2$N), 5.00 (s, 2H, COCH$_2$N), 7.46-8.96 (m, 9H, ArH, pyridine-H).

Example 12

IV-12 $N^1$-(4-aminobenzyl)-$N^4$-phenacyl piperazine trihydrochloride

This compound is defined in Formula I, wherein $R_1$ and $R_2$, each represents hydrogen; X represents amido; $Ar_1$=4-animophenyl, $Ar_2$=phenyl; n=m=1.

A mixture of N-(4-nitrobenzyl)piperazine dihydrochloride (10 g, 34 mmol), 2-chloro-1-phenylethanone (5.80 g, 37 mmol) and anhydrous $K_2CO_3$ (16.5 g, 119 mmol) was treated according to general preparation 2 to give 10.51 g of $N^1$-(4-nitrobenzyl)-$N^4$-phenacyl piperazine dihydrochloride (A), yield 75%, mp 236-8° C.

Reductive iron (6.5 g, 116 mmol) was mixed in 110 ml of 5% $NH_4Cl$, stirred for 40 minutes at 95° C., and cooled to 50° C. A (15.76 mmol) and 20 ml of water were added and stirred for 5 hours at 50° C. The mixture was adjusted to pH=9 with solid $K_2CO_3$, $CHCl_3$ (100 ml) was added and stirred for 30 minutes, then filtered, and washed with $CHCl_3$ (50 ml) and water (50 ml). The aqueous phase was extracted with $CHCl_3$ (50 ml×2), the combined organic phase was washed with saturated NaCl solution, dried (mGSO$_4$), filtrated, and then the solvent evaporated to dryness. The residue was dissolved in isopropanol, pH adjusted to 3 with HCl/$C_2H_5OH$. The resultant precipitate was recrystallized with ethanol to give 4.5 g of compound (IV-12), yield 68%, mp 194-196° C. (dec). Purity (HPLC): 99.70%, M+ 309.

Elementary analysis: $C_{19}H_{23}N_3O.3HCl$. Experimental: (% C, 52.10; H, 6.59; N, 9.72); theoretical value (% C, 52.24; H, 6.46; N, 9.58). IR (KCl): ν 3400, 2800, 1690, 1615, 1590, 1510 cm$^{-1}$. $^1$HNMR (DMSO-d6): δ 3.58 (m, 8H, piperazine-H), 4.45 (s, 2H, PhCH$_2$N), 5.25 (s, 2H, COCH$_2$N), 7.40-8.05 (m, 10H, ArH).

Example 13

IV-13 $N^1$-(4-aminobenzyl)-$N^4$-(1-benzoylethyl)piperazine trihydrochloride

A mixture of N-(4-nitrobenzyl)piperazine dihydrochloride (7.73 g, 26.3 mmol), 2-bromo-1-phenylpropan-1-one (5.94 ml, 39 mmol) and $K_2CO_3$ (12.7 g, 92 mol) was treated according to general preparation 2, then recrystallized with ethanol to give 85 g of $N^1$-(4-nitrobenzyl)-$N^4$-(1-benzoyl-ethyl)piperazine dihydrochloride, yield 70%, mp 256-8° C., which was reduced by reductive iron in the similar procedure of Example 12, to give compound (IV-13), yield 65%, mp 244-246° C. (dec). $M^+$ 323.

Elementary analysis: $C_{20}H_{25}N_3O.3HCl.2H_2O$. Experimental: (% C, 51.33; H, 6.84; N, 9.14); theoretical value (% C, 51.24; H, 6.88; N, 8.96). $^1$HNMR (DMSO-d6): δ 1.42 (d, 3H, CHCH$_3$), 3.39 (m, 8H, piperazine-H), 4.45 (s, 2H, PhCH$_2$N), 5.10 (m, 1H, COCHN), 7.40-8.05 (m, 10H, ArH).

Example 14

IV-14 $N^1$-phenethyl-$N^4$-phenacyl piperazine dihydrochloride

A mixture of N-phenethyl piperazine dihydrochloride (0.8 g, 3.04 mmol), 2-chloro-1-phenylethanone (0.56 g, 3.65 mmol), KHCO$_3$ (0.97 g, 9.7 mmol) and hexadecyl-trimethyl ammonium bromide (CTAB) (35 mg, 0.09 mmol) in H$_2$O/CHCl$_3$ (5 ml/18 ml) was treated according to general preparation 2 to give 0.73 g of compound (IV-14) as white solid, yield 60.33%, mp 238-240° C. $M^+$ 308.

Elementary analysis: $C_{20}H_{24}N_2O.2HCl.H_2O$. Experimental: (% C, 59.94; H, 7.50; N, 6.81); theoretical value (% C, 60.15; H, 7.07; N, 7.02). IR (KCl): ν 2980, 1690, 1630, 1590, 1570 cm$^{-1}$. $^1$HNMR (DMSO-d6): δ3.07 (m,4H, PhCH$_2$CH$_2$N), 3.60 (m,8H, piperazine-H), 5.16 (s,2H, NCH$_2$—CO), 7.26-8.02 (m, 10H, ArH).

Example 15

IV-15 $N^1$-(2,5-dimethoxybenzyl)-$N^4$-phenacyl piperazine dihydrochloride

A mixture of N-phenacyl piperazine dihydrochloride (1.5 g, 5 mmol), 1,4-di-methoxybenzylchloride (1.5 g, 8 mmol), KHCO$_3$ (1.73 g, 17 mmol) and CTAB (60 mg, 0.02 mmol) in H$_2$O/CHCl$_3$ (5 ml/18 ml) was treated according to general preparation 2 to give 0.73 g of compound (IV-15), yield 60.33%, mp 238-240° C. $M^+$ 354.

Elementary analysis: $C_{21}H_{26}N_2O_3.2HCl.1/2H_2O$. Experimental: (% C, 57.54; H, 6.71; N, 6.33); theoretical value (% C, 57.8; H, 6.71; N, 6.33).

Example 16

IV-16 $N^1$-benzyl-$N^4$-(4-aminophenacyl)piperazine trihydrochloride $N^1$-benzyl-$N^4$-(4-nitrophenacyl)piperazine dihydrochloride (IV-9) (2 mmol) was reduced by reductive iron in a procedure similar to Example 12 to give compound (IV-16), yield 60%, mp 286-288° C. $M^+$ 309.

Elementary analysis: $C_{19}H_{23}N_3O.3HCl.2H_2O$. Experimental: (% C, 49.44; H, 6.61; N, 9.13); theoretical value (% C, 49.35; H, 6.54; N, 9.09).

Example 17

IV-17 $N^1$-benzyl-$N^4$-benzoylethyl piperazine dihydrochloride

A mixture of N-benzyl piperazine dihydrochloride (4.93 g, 20 mmol), 3-chloro-1-phenylpropan-1-one (4 g, 24 mmol), KOH (3.6 g, 64 mmol) and CTAB (0.23 g, 0.6 mmol) in H$_2$O/CHCl$_3$ (20 ml/40 ml) was treated according to general preparation 2 to give 5.49 g of compound (IV-17), yield 72%, mp 230-232° C. $M^+$ 308.

Elementary analysis: $C_{20}H_{24}N_2O.2HCl$. Experimental: (% C, 62.97; H, 6.93; N, 7.31); theoretical value (% C, 62.99; H, 6.87; N, 7.35). IR (KCl): ν 2980, 1675, 1600, 1580 cm$^{-1}$. $^1$HNMR (DMSO-d$_6$): δ 3.37-3.41 (m, 4H, NCH$_2$CH$_2$CO), 3.55 (m, 8H, piperazine-H), 4.05 (s, 2H, PhCH$_2$N), 7.43-7.95 (m, 10H, ArH).

Example 18

IV-18 $N^1$-(4-nitrobenzyl)-$N^4$-[(4-acetamido)phenacyl]piperazine dihydrochloride A mixture of N-(4-nitrobenzyl)piperazine dihydrochloride (2.94 g, 10 mmol), N-[4-(2-chloroacetyl)phenyl]acetamide (2.37 g, 12 mmol) and anhydrous K$_2$CO$_3$ (4.83 g, 35 mmol) was treated according to general preparation 2 to give compound (IV-18), yield 74%, mp 228-230° C. $M^+$ 396.

Elementary analysis: $C_{21}H_{24}N_4O_4.2HCl.3/2H_2O$. Experimental: (% C, 50.81; H, 5.89; 11.35); theoretical value (% C, 50.81; H, 5.89; N, 11.35).

Example 19

IV-19 $N^1$-(3,4-methylenedioxybenzyl)-$N^4$-benzoylethyl piperazine dihydrochloride A mixture of N-(3,4-methylenedioxobenzyl)piperazine dihydrochloride (3 g, 13.62 mmol), 2-chloro-1-phenylethanone (2.32 g, 14.98 mmol) and anhydrous K$_2$CO$_3$ (2.82 g, 20.43 mmol) was treated according to general preparation 2 to give 3.90 g of compound (IV-19) as white solid, yield 68%, mp 240-241° C. $M^+$ 338.

Elementary analysis: $C_{20}H_{22}N_2O_3.2HCl.1/2H_2O$. Experimental: (% C, 57.59; H, 5.87; N, 6.39); theoretical value (% C, 57.15; H, 6.00; N, 6.67).

IR (KCl): ν 2940, 1700, 1600, 1580, 1500 cm$^{-1}$

Example 20

IV-20 $N^1$-(4-fluorobenzyl)-$N^4$-(4-chlorophenacyl)piperazine dihydrochloride

A mixture of N-(4-chlorobenzyl)piperazine dihydrochloride (2 g, 7.5 mmol), 2-bromo-1-(4-chlorophenyl)ethanone (2.1 g, 9 mmol), KOH (1.34 g, 24 mmol) and CTAB (85 mg, 0.22 mmol) in H$_2$O/CHCl$_3$ (5 ml/18 ml) was treated according to general preparation 2 to give 1.8 g of compound (IV-20), yield 54.87%, mp 246-248° C. (dec). $M^+$ 346.

Elementary analysis: $C_{19}H_{20}FClN_2O.2HCl.H_2O$. Experimental: (% C, 52.50; H, 5.12; N, 6.07); theoretical value (% C, 52.13; H, 5.52; N, 6.40).

IR (KCl): ν 2900, 1700, 1590, 1510 cm$^{-1}$.

$^1$HNMR (DMSO-d6): δ 3.64 (m, 8H, piperazine-H), 4.45 (s, 2H, PhCH$_2$), 5.12 (br, 2H, NCH$_2$CO), 7.29-8.03 (m, 8H, ArH).

Example 21

IV-21 $N^1$-(4-acetamidobenzyl)-$N^4$-benzoylethyl piperazine dihydrochloride

A mixture of N-benzoylethyl piperazine dihydrochloride (1.5 g, 5 mmol), 4-acetamino-benzylchloride (1.1 g, 6 mmol) and K$_2$CO$_3$ (3.2 g, 24 mmol) in 60 ml of acetone was treated according to general preparation 2 to give compound (IV-21) yield 65%, mp 238-240° C. M⁺ 351.

Elementary analysis: $C_{21}H_{25}N_3O_2 \cdot 2HCl \cdot 1/2H_2O$. Experimental: (% C, 57.81; H, 6.44; N, 9.45); theoretical value (% C, 58.20; H, 6.51; N, 9.70).

Example 22

IV-22 $N^1$-(3-phenylpropyl-3-ol)-$N^4$-(4-methoxy phenacyl)piperazine dihydrochloride A mixture of N-(3-phenylpropyl-3-ol)piperazine dihydrochloride (1.5 g, 6.75 mmol), 2-bromo-1-(4-methoxyphenyl)ethanone (1.7 g, 7.4 mmol) and $K_2CO_3$ (3.3 g, 24 mmol) in 60 ml of acetone, was treated according to general preparation 2 to give compound (IV-22), yield 54%, mp 240-243° C. M⁺ 368.

Elementary analysis: $C_{22}H_{28}N_2O_3 \cdot 2HCl$. Experimental: (% C, 60.21; H, 7.03; N, 6.31); theoretical value (% C, 59.86; H, 6.85; N, 6.35). IR (KCl): ν 2900, 1700, 1590, 1510 cm⁻¹. ¹HNMR (DMSO-d6): δ 3.69 (m, 8H, piperazine-H), 3.82 (3H, OCH₃), 5.10 (s, 1H, PhCH), 7.10-7.13 (d, 4H, ArH), 7.17-7.23 (m, 5H, ArH).

Example 23

IV-23 $N^1$-(2-methoxy-5-nitrobenzyl)-$N^4$-phenacyl piperazine dihydrochloride

A mixture of N-phenacyl piperazine dihydrochloride (1.7 g, 6.1 mmol), 2-methoxy-5-nitro-benzylbromide (1.5 g, 6.1 mmol) and $K_2CO_3$ (2.7 g, 19.5 mmol) in 40 ml of acetone was treated according to general preparation 2 to give 1.80 g of compound (IV-23), yield 60%. M⁺ 368.

Elementary analysis: $C_{20}H_{23}N_3O_4 \cdot 2HCl$. Experimental: (% C, 49.02; H, 5.93; N, 8.76); theoretical value (% C, 49.28; H, 6.20; N, 8.62).

Example 24

IV-24 $N^1$-[1-(4-fluorophenyl)ethyl]-$N^4$-phenacyl piperazine dihydrochloride

A mixture of N-phenacyl piperazine dihydrochloride (1.39 g, 5 mmol), 1-(1-chloroethyl)-4-fluorobenzene (0.95 g, 6 mmol) and $K_2CO_3$ (2.42 g, 17.5 mmol) in 40 ml of acetone was treated according to general preparation 2 to give 1.25 g of compound (IV-24), yield 61%. M⁺ 326.

Elementary analysis: $C_{20}H_{23}FN_2O \cdot 2HCl \cdot 1/2H_2O$. Experimental: (% C, 58.70; H, 6.53; N, 6.66); theoretical value (% C, 58.83; H, 6.42; N, 6.86).

Example 25

IV-25 $N^1$-(3-methoxybenzyl)-$N^4$-phenacyl piperazine dihydrochloride

A mixture of 3-methoxybenzylchloride (0.5 g, 2.15 mmol), N-phenacyl piperazine dihydrochloride (0.6 g, 2.15 mmol) and $K_2CO_3$ (1.04 g, 7.52 mmol) in 30 ml of acetone was treated according to general preparation 2 to give 0.46 g of compound (IV-25), yield 54%. M⁺ 324.

Elementary analysis: $C_{20}H_{24}N_2O_2 \cdot 2HCl$. Experimental: (% C, 60.22; H, 6.43; N, 7.26); theoretical value (% C, 60.45; H, 6.66; N, 7.05).

Example 26

IV-26 $N^1$-[(2-benzenesulfonylmethyl)benzyl]-$N^4$-phenacyl piperazine dihydrochloride A mixture of (2-benzenesulfonylmethyl)-benzyl bromide (0.5 g, 1.54 mmol), N-phenacyl piperazine dihydrochloride (0.32 g, 1.54 mmol) and $K_2CO_3$ (0.74 g, 5.38 mmol) in 40 ml of acetone was treated according to general preparation 2 to give 0.4 g of compound (IV-26), yield 50%. M⁺ 448.

Elementary analysis: $C_{26}H_{28}N_2O_3S \cdot 2HCl$. Experimental: (% C, 60.02; H, 5.98; N, 5.46); theoretical value (% C, 59.88; H, 5.80; N, 5.37).

Example 27

IV-27 $N^1$-[1-(4-nitrophenyl)ethyl]-$N^4$-(4-methylphenacyl)piperazine dihydrochloride A mixture of N-[1-(4-nitrophenyl)ethyl]piperazine (4 g, 13 mmol), 2-bromo-1-(4-methylphenyl)ethanone (3.32 g, 15.57 mmol) and $K_2CO_3$ (6.28 g, 45.42 mmol) in 150 ml of DMF was treated according to general preparation 2 to give 3.77 g of compound (IV-27), yield 65.8%. M⁺ 369.

Elementary analysis: $C_{21}H_{25}N_3O_3 \cdot 2HCl$. Experimental: (% C, 57.02; H, 5.98; N, 10.26); theoretical value (% C, 57.27; H, 6.18; N, 10.42).

Example 28

IV-28 $N^1$-benzyl-$N^4$-(5-chloro-6-methoxy-2-naphthoylmethyl)piperazine dihydrochloride A mixture of N-benzylpiperazine dihydrochloride (2 g, 9.4 mmol), 2-bromo-1-(5-chloro-6-methoxynaphthalen-2-yl)ethanone (1.50 g, 6 mmol) and $K_2CO_3$ (2.07 g, 15 mmol) in 120 ml of acetone was treated according to general preparation 2 to give 2.85 g of compound (IV-28), yield 74.82%, mp 241° C. (dec). M⁺ 344.

Elementary analysis: $C_{23}H_{24}N_2O \cdot 2HCl \cdot H_2O$. Experimental: (% C, 66.58; H, 6.29; N, 6.57); theoretical value (% C, 66.19; H, 6.24; N, 6.71). IR (KCl): ν 2900, 1700, 1630, 1600 cm⁻¹. ¹HNMR (DMSO-d6): δ3.57 (m, 8H, piperazine-H), 4.48 (s, 2H, PhCH₂), 5.33 (s, 2H, NCH₂CO), 7.46-8.14 (m, 12H, ArH).

Example 29

IV-29 $N^1$-benzyl-$N^4$-[1-(5-chloro-6-methoxy-2-naphthoyl)ethyl]piperazine dihydrochloride A mixture of N-benzyl piperazine dihydrochloride (1.5 g, 7.05 mmol), 2-bromo-1-(5-chloro-6-methoxynaphthalen-2-yl)propan-1-one (2.8 g, 8.5 mmol) and triethylamine (2.38 g, 23.5 mmol) in 150 ml of benzene was treated according to general preparation 2 to give 2.14 g of compound (IV-29), yield 60%, mp 252-253° C. (dec). M⁺ 423.

Elementary analysis: $C_{25}H_{27}N_2O_2Cl \cdot 2HCl \cdot H_2O$. Experimental: (% C, 59.60; H, 5.81; N, 5.44); theoretical value (% C, 59.46; H, 5.49; N, 5.55) ¹HNMR (DMSO-d6):

Example 30

IV-30 $N^1$-(3,4-methylenedioxybenzyl)-$N^4$-[1-(5-chloro-6-methoxy-2-naphthoyl) ethyl]piperazine dihydrochloride A mixture of N-(3,4-methylenedioxobenzyl)piperazine dihydrochloride (1 g, 4.5 mmol), 2-chloro-1-(5-chloro-6-methoxynaphthalen-2-yl)propan-1-one (1.54 g, 5.4 mmol) and $K_2CO_3$ (1.57 g, 11.25 mmol) in 20 ml of DMF, was treated according to general preparation 2 to give 0.62 g of compound (IV-30), yield 70%, mp 230-232° C. $M^+$ 466.

Elementary analysis: $C_{26}H_{27}ClN_2O_4.2HCl$. Experimental: (% C, 57.63; H, 5.37; N, 5.44); theoretical value (% C, 57.84; H, 5.04; N, 5.19).

Example 31

IV-31 $N^1$-(4-methoxybenzyl)-$N^4$-[1-(5-chloro-6-methoxy-2-naphthoyl)ethyl]piperazine dihydrochloride A mixture of N-(4-methoxybenzyl)piperazine dihydrochloride (0.35 g, 1.3 mmol), 2-chloro-1-(5-chloro-6-methoxynaphthalen-2-yl)propan-1-one (0.44 g, 1.57 mmol) and $K_2CO_3$ (0.65 g, 4.6 mmol) in 20 ml of DMF was treated according to general preparation 2 to give 0.4 g of compound (IV-31), yield 57%, mp 222-224° C. $M^+$ 452.

Elementary analysis: $C_{26}H_{29}ClN_2O_3.2HCl.H_2O$. Experimental: (% C, 59.10; H, 5.66; N, 5.39); theoretical value (% C, 59.38; H, 5.94; N, 5.33).

Example 32

IV-32 $N^1$-(4-nitrobenzyl)-$N^4$-[1-(5-chloro-6-methoxy-2-naphthoyl)ethyl]piperazine dihydrochloride A mixture of N-(4-nitrobenzyl)piperazine dihydrochloride (2.94 g, 10 mmol), 2-bromo-1-(5-chloro-6-methoxynaphthalen-2-yl)propan-1-one (3.93 g, 12 mmol) and $K_2CO_3$ (4.83 g, 35 mmol) in 50 ml of DMF was treated according to general preparation 2 to give 3.51 g of compound (IV-32), yield 65%. $M^+$ 467.

Elementary analysis: $C_{25}H_{26}ClN_3O_4.2HCl$. Experimental: (% C, 55.42; H, 5.46; N, 7.59); theoretical value (% C, 55.52; H, 5.22; N, 7.77).

Example 33

IV-33 $N^1$-(4-aminobenzyl)-$N^4$-[1-(5-chloro-6-methoxy-2-naphthoyl)ethyl]piperazine dihydrochloride A mixture of reductive iron (0.36 g, 6.47 mmol) in 8.5 ml of 5% $NH_4Cl$, $N^1$-(4-nitrobenzyl)-$N^4$-[1-(5-chloro-6-methoxy-2-naphthoyl)ethyl]piperazine (IV-32) (0.5 g, 0.92 mmol) and water (10 ml) was stirred for 5 hours, and processed according to the procedure of example 12 to give 0.27 g of compound (IV-33), yield 60%, mp 206-8° C., $M^+$ 437.

Elementary analysis: $C_{25}H_{28}ClN_3O_2.2HCl$. Experimental: (% C, 59.01; H, 5.96; N, 8.39); theoretical value (% C, 58.77; H, 5.91; N, 8.23).

Example 34

IV-34 $N^1$-(3,4,5-trimethoxybenzyl)-$N^4$-[1-(5-chloro-6-methoxy-2-naphthoyl) ethyl]piperazine dihydrochloride A mixture of $N^1$-(3,4,5-trimethoxybenzyl)piperazine dihydrochloride (0.9 g, 2.7 mmol), 2-bromo-1-(5-chloro-6-methoxynaphthalen-2-yl)propan-1-one (1.05 g, 3.2 mmol) and $K_2CO_3$ (1.3 g, 9.5 mmol) in 25 ml of DMF was treated according to general preparation 2 to give 1.15 g of compound (IV-34), yield 72.7%, mp 219-222° C., $M^+$ 512.

Elementary analysis: $C_{28}H_{33}ClN_2O_5.2HCl$. Experimental: (% C, 57.10; H, 5.99; N, 4.73); theoretical value (% C, 57.39; H, 6.04; N, 4.80).

Example 35

IV-35 $N^1$-Cinnamyl-$N^4$-[1-(5-chloro-6-methoxy-2-naphthoyl)ethyl]piperazine dihydrochloride A mixture of N-cinnamyl piperazine dihydrochloride (2.75 g, 10 mmol), 2-bromo-1-(5-chloro-6-methoxynaphthalen-2-yl)propan-1-one (1.05 g, 3.2 mmol) and $K_2CO_3$ (1.3 g, 9.5 mmol) in 50 ml of $CHCl_3$ was treated according to general preparation 2 to give 3.65 g of compound (IV-35), yield 70%. $M^+$ 449.

Elementary analysis: $C_{27}H_{29}ClN_2O_2.2HCl$. Experimental: (% C, 62.10; H, 5.98; N, 5.33); theoretical value (% C, 62.13; H, 5.99; N, 5.37).

Example 36

IV-36 $N^1$-(3-chlorobenzyl)-$N^4$-[1-(5-chloro-6-methoxy-2-naphthoyl)ethyl]piperazine dihydrochloride A mixture of N-(3-chlorobenzyl)piperazine dihydrochloride (1.35 g, 5 mmol), 2-bromo-1-(5-chloro-6-methoxynaphthalen-2-yl)propan-1-one (1.96 g, 6 mmol) and $K_2CO_3$ (2.42 g, 17.5 mmol) in 40 ml of DMF was treated according to general preparation 2 to give 1.65 g of compound (IV-36), yield 64%. $M^+$ 444.

Elementary analysis: $C_{24}H_{24}Cl_2N_2O_2.2HCl$. Experimental: (% C, 55.60; H, 5.28; N, 5.33); theoretical value (% C, 55.83; H, 5.08; N, 5.43).

Example 37

IV-37 $N^1$-(1-phenylethyl)-$N^4$-phenacyl piperazine dihydrochloride

A mixture of N-(1-phenethyl)piperazine dihydrochloride (2 g, 8.8 mmol), 2-chloro-1-phenylethanone (1.67 g, 11 mmol) and triethylamine (2.22 g, 22 mmol) in 80 ml of benzene was treated according to general preparation 2 to give 2.3 g of compound (IV-37) as white solid, yield (67.5%), mp 242° C. (dec), $M^+$ 308.

Elementary analysis: $C_{20}H_{24}N_2O.2HCl$. Found: (% C, 62.43; H, 6.88; N, 6.91); theoretical value (% C, 62.99; H, 6.82; N, 7.35).

Example 38

IV-38 $N^1$—(R-1-phenylethyl)-$N^4$-phenacyl piperazine dihydrochloride

(1) N—(R-1-phenylethyl)piperazine dihydrochloride

A mixture of chloroacetic acid (94.5 g) and 32.2 ml of R-1-phenylethylamine in 125 ml of 8N NaOH was reacted at 70° C. for 10 hours, and a solution of $BaCl_2$ (65 g) in 200 ml of water was added dropwise, and then the mixture was refluxed for 1 hour. After filtration, the solid was put into 400 ml of water and then 100 ml of 5N $H_2SO_4$ added, the mixture was refluxed for 1 hour, filtered and washed with water. The filtrate was evaporated in vacuo to give N,N-di(hydroxyformyl)-(R)-1-phenylethylamine.

A mixture of the above product and 80 ml of formamide in 80 ml of Xylene was refluxed for 8 hours, and then extracted with EtOAC (100 ml×2). The combined organic phase was washed with water, concentrated in vacuo to obtain (R)-4-(1-phenylethyl)piperazine-2,6-dione as colorless crystals. Yield 72% (two steps).

A mixture of (R)-4-(1-phenylethyl)piperazine-2,6-dione (10.9 g, 50 mmol) and $LiAlH_4$ (4.75 g, 125 mmol) in 150 ml of THF was refluxed for 2 hours, $Na_2SO_4$ (6 g) added, and stirred for 1 hour, filtered and washed with EtOAC. The filtrate was adjusted to pH=2 with $HCl/C_2H_5OH$. The resulting precipitate was recrystallized from ethanol to give N—(R-1-phenylethyl)piperazine dihydrochloride, yield 85%, $[\alpha]^{20}_D$ +22.40° (c=1, MeOH).MS: m/z 190 (M+).

(2) $N^1$—(R-1-phenylethyl)-$N^4$-phenacyl piperazine dihydrochloride

A mixture of N—(R-1-phenylethyl)piperazine dihydrochloride (0.26 g, 10 mmol), 2-chloro-1-phenylethanone (0.232 g, 15 mmol) and $K_2CO_3$ (0.414 g, 30 mmol) in acetone was treated according to general preparation 2 to give 0.28 g of compound (IV-38) as white solid, mp: 230-232° C. $[\alpha]^{20}_D$ +21.970 (c=1, MeOH), $M^+$ 308.

Elementary analysis: $C_{20}H_{24}N_2O.2HCl.H_2O$, Experimental: (% C, 60.47; H, 6.82; N, 7.06); theoretical value (% C, 60.28; H, 7.09; N, 7.03). IR (KBr): ν 3400, 2940, 1685, 1450, 760, 690 $cm^{-1}$. $^1$HNMR (DMSO-$d_6$): δ1.70-1.72 (d, 3H, $CH_3$), 3.37-3.55 (m, 8H, piperazine-H), 4.60-4.65 (m, 1H, NCH), 5.03 (s, 2H, $NCH_2CO$), 7.48-7.97 (m, 10H, ArH).

Example 39

IV-39 $N^1$-(S-1-phenylethyl)-$N^4$-phenacyl piperazine dihydrochloride

N—(S-1-phenylethyl)piperazine dihydrochloride was prepared first according to Example 38 by using (S)-1-phenylethylamine as a starting material, $[\alpha]^{20}_D$ –22.50° (c=1, MeOH). A mixture of N—(S-1-phenylethyl)piperazine dihydrochloride (0.26 g, 10 mmol), 2-chloro-1-phenylethanone (0.232 g, 15 mmol) and $K_2CO_3$ (0.414 g, 30 mmol) in acetone was treated according to general preparation 2 to give 0.30 g of compound (IV-39) as white solid, mp: 236-238° C., $[\alpha]^{20}_D$ –22.55° (c=1, MeOH), $M^+$ 308.

Elementary analysis: $C_{20}H_{24}N_2O.2HCl.H_2O$. Experimental: (% C, 61.91; H, 6.85; N, 7.20); theoretical value (% C, 61.54; H, 6.92; N, 7.18). IR (KBr): ν 3400, 2950, 1690, 1450, 760, 690 $cm^{-1}$. $^1$HNMR (DMSO-d6): δ1.70-1.72 (d, 3H, $CH_3$), 3.37-3.55 (m, 8H, piperazine-H), 4.60-4.65 (m, 1H, NCH), 5.03 (s, 2H, $NCH_2CO$), 7.48-7.97 (m, 10H, ArH).

Example 40

IV-40 $N^1$-(1-phenylethyl)-$N^4$-(4-methyl phenacyl) piperazine dihydrochloride A mixture of N-(1-phenylethyl)piperazine dihydrochloride (4.07 g, 15 mmol), 2-bromo-1-(4-methylphenyl)ethanone (3 g, 14 mmol) and $K_2CO_3$ (6.81 g, 49 mmol) in 60 ml of DMF was treated according to general preparation 2 to give 2.51 g of compound (IV-40) as white solid, mp: 230-232° C. $M^+$ 308.

Elementary analysis: $C_{21}H_{26}N_2O.2HCl.1/2H_2O$. Experimental: (% C, 63.47; H, 7.37; N, 7.06); theoretical value (% C, 63.80; H, 7.14; N, 7.09). IR (KBr): ν 3400, 2940, 1685, 1450, 760, 690 $cm^{-1}$. $^1$HNMR (DMSO-d6): 81.70-1.72 (d, 3H, $CH_3$), 3.37-3.55 (m, 8H, piperazine-H), 4.60-4.65 (m, 1H, NCH), 5.03 (s, 2H, $NCH_2CO$), 7.48-7.97 (m, 10H, ArH).

Example 41

IV-41 $N^1$—(R-1-phenylethyl)-$N^4$-(4-methyl phenacyl)piperazine dihydrochloride A mixture of 2-bromo-1-(4-methylphenyl)ethanone (0.263 g, 1 mmol), N—(R-1-phenylethyl)piperazine dihydrochloride (0.23 g, 1.1 mmol) and $K_2CO_3$ (0.414 g, 3 mmol) in acetone was treated according to general preparation 2 to give 0.36 g of compound (IV-41) as white solid, mp: 231-232° C. $[\alpha]^{27}_D$ +15.230 (c=1, MeOH). $M^+$ 322.

Elementary analysis: $C_{21}H_{26}N_2O.2HCl.H_2O$. Experimental: (% C, 61.10; H, 7.02; N, 6.75); theoretical value (% C, 61.16; H, 7.09; N, 6.80). IR (KBr): ν 3440, 2965, 1685, 1435, 810, 710 $cm^{-1}$. $^1$HNMR (DMSO-d6+$D_2O$): δ1.67-1.68 (d, 3H, $CH_3$), 2.37 (s, 3H, Ar—$CH_3$), 3.29-3.54 (m, 8H, piperazine-H), 4.52-4.57 (m, 1H, NCH), 4.88 (s, 2H, $NCH_2CO$), 7.37-7.85 (m, 9H, ArH).

Example 42

IV-42 $N^1$-(S-1-phenylethyl)-$N^4$-(4-methyl phenacyl) piperazine dihydrochloride A mixture of 2-bromo-1-(4-methylphenyl)ethanone (0.526 g, 2 mmol), N—(S-1-phenylethyl)piperazine dihydrochloride (0.46 g, 2.2 mmol) and $K_2CO_3$ (0.828 g, 6 mmol) in acetone was treated according to general preparation 2 to give 0.7 g of compound (IV-42) as white solid, mp: 236-238° C. $[\alpha]^{27}_D$ –15.01° (c=1, MeOH), $M^+$ 322.

Elementary analysis: $C_{21}H_{26}N_2O.2HCl.H_2O$. Experimental: (% C, 61.10; H, 7.21; N, 6.60); theoretical value (% C, 61.06; H, 7.09; N, 6.80) IR (KBr): ν 3440, 2960, 1685, 1435, 810, 710 $cm^{-1}$. $^1$HNMR (DMSO-d6+$D_2O$): δ1.67-1.68 (d, 3H, $CH_3$), 2.37 (s,3H, Ar—$CH_3$), 3.29-3.54 (m, 8H, piperazine-H), 4.52-4.57 (m, 1H, NCH), 4.88 (s, 2H, $NCH_2CO$), 7.37-7.85 (m, 9H, ArH).

Example 43

IV-43 $N^1$-phenylethyl-$N^4$-[1-(5-chloro-6-methoxy-2-naphthoyl)ethyl]piperazine dihydrochloride

A mixture of N-(1-phenylethyl)piperazine dihydrochloride (0.79 g, 3 mmol), 2-bromo-1-(5-chloro-6-methoxynaphthalen-2-yl)propan-1-one (1.64 g, 5 mmol) and $K_2CO_3$ (1.38 g, 10 mmol) in acetone was treated according to general preparation 2 to give 1.06 g of compound (IV-43) as white solid, yield 65%, mp 231-232° C. $M^+$ 437.

Elementary analysis: $C_{26}H_{29}ClN_2O_2.2HCl.2H_2O$. Experimental: (% C, 57.37; H, 6.37; N, 5.06); theoretical value (% C, 57.20; H, 6.46; N, 5.13)

Example 44

IV-44 $N^1$-(S-1-phenylethyl)-$N^4$-[1-(5-chloro-6-methoxy-2-naphthoyl)ethyl]piperazine dihydrochloride

A mixture of $N^1$-(S-1-phenylethyl)piperazine dihydrochloride (2.63 g, 10 mmol), 2-bromo-1-(5-chloro-6-methoxynaphthalen-2-yl)propan-1-one (3.6 g, 11 mmol) and $K_2CO_3$ (4.83 g, 35 mmol) in acetone was treated according to general preparation 2 to give 2.7 g of compound (IV-44) as white solid. $M^+$ 437.

Elementary analysis: $C_{26}H_{29}ClN_2O_2.2HCl$. Experimental: (% C, 61.47; H, 5.47; N, 5.36); theoretical value (% C, 61.24; H, 5.73; N, 5.50).

Example 45

IV-45 $N^1$—(R-1-phenylethyl)-$N^4$-[1-(5-chloro-6-methoxy-2-naphthoyl)ethyl]piperazine dihydrochloride

The title compound (2.9 g) was prepared in a procedure similar to Example 44 by using N—(R-1-phenylethyl)piperazine dihydrochloride (2.63 g, 10 mmol) as a starting material. $M^+$ 437.

Elementary analysis: $C_{26}H_{29}ClN_2O_2.2HCl$. Experimental: (% C, 61.31; H, 5.42; N, 5.41); theoretical value (% C, 61.24; H, 5.73; N, 5.50).

Example 46

| | |
|---|---|
| Tablet: The compound in this invitation | 25 mg |
| Sucrose | 155 mg |
| Corn starch | 65 mg |
| Magnesium stearate | 5 mg |

Preparation: A mixture of the active ingredient, sucrose and corn starch in water was well stirred, and then dried and sifted, which was mixed with Megnesium stearate evenly, and tableted. Each tablet is 250 mg, which containing 25 mg of the compound.

Example 47

| | |
|---|---|
| Injection: The compound in this invitation | 10 mg |
| Physiological saline | 90 mg |

Preparation: The active ingredient was dissolved in physiological saline, and then mixed evenly and filtered. The clear solution so-obtained was filled separately into ampoules under aseptic condition, and the composition of each ampoule weighs 10 mg, which containing 1 mg of the compound.

Example 48

The Analgesic and Sedative Effects of the Compounds In Vivo

1. Analgesic and Sedative Effect in Mice Writhing Model

Kunming mice were used, with a male-female ratio of 50-50%. The test compound is administered i.p. (20 mg/Kg body weight) to the test groups, and physiological saline is administered P.O. (20 ml/Kg body weight) to the control group. After 30 minutes, acetic acid (0.7%, 10 mg/kg i.p.) was injected and the number of writhes was observed during a 5-minute period after acetic acid administration. The inhibition ratio of the writhing threshold was calculated. The alternating current tube is used to record the spontaneous activities for measuring sedation. Results are shown in Table 2.

TABLE 2

| | Analgesia | Sedation | | Analgesia | Sedation | | Analgesia | Sedation |
|---|---|---|---|---|---|---|---|---|
| IV-1 | 68.2% | 65.6% | IV-3 | 56.6% | 70.8% | IV-4 | 93.2% | 39.6% |
| IV-5 | 14 | 44 | IV-6 | 43 | 73 | IV-7 | 25 | 43 |
| IV-8 | 39 | 64 | IV-9 | 74 | 32 | IV-10 | 100 | 99 |
| IV-11 | 86 | 91 | IV-12 | 100 | 97 | IV-13 | 100 | 86 |
| IV-14 | 94 | 92 | IV-15 | 80 | 93 | IV-16 | 63 | 51 |
| IV-17 | 45 | 75 | IV-18 | 64 | 65 | IV-19 | 97 | 93 |
| IV-20 | 45 | 60 | IV-21 | 100 | 92 | IV-22 | 100 | 84 |
| IV-23 | 87 | 96 | IV-24 | 64 | 47 | IV-25 | 100 | 88 |
| IV-27 | 57 | 74 | IV-31 | 45 | 7 | IV-37 | 100 | 90.1 |
| IV-38 | 51 | 99 | VI-39 | 42 | 35 | IV-41 | 60 | 72 |
| IV-42 | 44 | 0 | VI-43 | 42 | 4 | IV-47 | 28.8 | 26.4 |
| IV-55 | 21 | 52 | IV-58 | 49 | 32 | IV-59 | 45 | 0 |
| IV-60 | 37 | 66 | IV-61 | 6 | 56 | IV-62 | 64 | 42 |

2. The Analgesic Effect in Rat Hot Plate Model

Using 55° C. hot plate pain threshold detector (available from Ninghai Baishi Electronic Medical Instrument Co., Zhejiang, China) the threshold change before and after administration of a pharmaceutical composition of the present invention is tested. Female mice's hind paw was scrubbed with alcohol cotton ball before the experiment. The regular pain threshold was tested twice for each rat, the induced hind paw licking time being recorded as the pain threshold. Measurements were made at 20-30 minute intervals. Only rats with stable pain reaction were used in the pharmaceutical test. The test compound is administered i.p. (20 mg/Kg) and an increase of the observed pain threshold by 100 percent or more indicates analgesic activity. Results are shown in Table 3.

TABLE 4

| Compound | Before (s) | After (s) | increase (s) | increase (%) | P value |
|---|---|---|---|---|---|
| IV-12 | 7.84 | 10.05 | 2.21 | 34% | 0.005 |
| IV-37 | 8.43 | 10.54 | 2.11 | 25% | 0.101 |
| IV-10 | 8.05 | 8.81 | 0.76 | 9.4% | 0.173 |
| IV-14 | 7.7 | 10.62 | 2.92 | 37.9% | 0.005 |
| IV-19 | 8.04 | 8.58 | 0.54 | 6.7% | 0.366 |
| IV-21 | 7.63 | 9.72 | 2.09 | 28% | 0.001 |
| IV-40 | 7.3 | 7.88 | 0.58 | 8% | 0.183 |
| IV-25 | 7.49 | 8.37 | 0.88 | 12% | 0.096 |
| IV-27 | 8.58 | 9.37 | 0.79 | 9.2% | 0.233 |

TABLE 5

| Compound 20 mg/kg | Increase (tail flick) (%) | P value | Increase (hot plate) (%) | Sedation | Writhing (K i) | Sedation |
|---|---|---|---|---|---|---|
| IV-12 | 34% | 0.005 | 100% | ++ | 100 | 97 |
| IV-14 | 37.9% | 0.005 | 100% | ++ | 94 | 92 |
| IV-21 | 28% | 0.001 | 100% | +++ | 100 | 92 |

TABLE 3

| Compound | Analgesic ratio (Increase by 100%) | Analgesic ratio (More than 60 seconds) | Sedation | Excitement |
|---|---|---|---|---|
| IV-12 | 100 | 80 | ++ | |
| IV-37 | 100 | 100 | +++ | |
| IV-10 | 90 | 70 | +++ | |
| IV-14 | 100 | 70 | ++ | |
| IV-19 | 70 | 50 | ++++ | |
| IV-21 | 100 | 50 | ++++ | |
| IV-40 | 10 | 10 | ± | |
| IV-25 | 40 | 10 | + | |
| IV-27 | 20 | 0 | no | no |

3. The Analgesic Effect in Rat Tail Flick Model

A 8.75 mm-projecting lamp (12 v, 50 w) was used to give out focused radiant heat. The terminal 3 cm of the tail is exposed to the heat. The intensity of the focused radiant heat is regulated by a transformer to ensure that the time required to elicit a tail flick response is within 3-5 seconds. The rat's pain threshold is pre-tested for 2-3 times; and only animals with stable reactions were used in the pharmaceutical test. The test substance is taken orally 20 mg/kg. The number of rats whose increase in time for eliciting a tail flick response is by 100% or more at the peak of the drug action (30-45 minutes after administration) is used to calculate analgesic effect. The results are shown in Table 4 and analysis of the results is in Table 5.

The results on all the three algogenic models show that IV-12 and IV-14 have powerful analgesic effects as well as a rather significant sedative effect. V-15 has shown great analgesic effect but no tendency of sedation. All the compounds mentioned above have profound for further value development.

Example 49

The Analgesic Pharmacological Studies of IV-12

1. The Analgesic Pharmacodynamics of IV-12

Two species of animals (mice and rats) and four types of pain testing models (i.p. 0.7% acetic acid, s.c. 5% formalin, hot plate 55° C., focused radiant heat) were used. The outcome confirmed that oral administration of IV-12 has an obvious analgesic effect, slightly weaker than Morphine and Bucinperazine, but significantly stronger than Aspirin and Paracetamol. Their $ED_{50}$ are shown in Table 6.

TABLE 6

| Compound | Animal | Method to test pain | Analgesia $ED_{50}$ (mg/kg p.o.) |
|---|---|---|---|
| IV-12 | Mice | Acetic acid Writhing | 13.2 |
| Aspirin | | | 348.0 |
| Paracetamol | | | 132.3 |
| Morphine | | | 6.8 |
| IV-12 | Mice | 55° C. Hot plate | 20.6 |
| Bucinperazine | | | 13.1 |
| Morphine | | | 7.7 |
| IV-12 | Rat | 5% Formalin paw s.c. | 102.0 |
| Aspirin | | | 2306.0 |
| IV-12 | Rat | 55° C. Hot plate | 52.4 |
| Aspirin | | | 843.0 |
| Paracetamol | | | 4320.0 |
| Morphine | | | 107.1 |
| IV-12 | | Tail flick | 161.9 |
| Aspirin | | | >5000 |
| Paracetamol | | | >5000 |
| Morphine | | | 23.3 |

2. Studies on the Analgesic Mechanism of IV-12

(1) Binding experiments with opioid μ-receptor in mouse brain indicated that IV-12 had a weak competitive binding with $^3$H-DAGO (the specific μ-receptor agonist). The Ki is $1.8\times10^{-9}$M (FIG. 1).

(2) The result of electrophysiology of the hippocampus's pyramidal cell showed that IV-12 is an antagonist that acts on the polyamine site of the NMDA receptor, which has the advantage of high selectivity as well as effects on a single site. The results are as follows:

a. IV-12 can reversibly suppress the current sensing induced by 100 μM NMDA, the $IC_{50}$ is 1.112±1.0 μM, and the Hill coefficient is 1.12. IV-12 did not affect the voltage-gating channel and the current sensing induced by AMPA and KA, indicating that IV-12 selectively suppresses the NMDA receptor.

b. Perfusion alone at 200 μM of IV-12 did not affect the electric current of resting membrane, suggesting that IV-12 has no intrinisic agonist activity. It displayed no tolerance after repeated administration. In addition, IV-12 did not affect the $EC_{50}$ of current sensing induced by NMDA, indicating that IV-12 is a non-competitive NMDA receptor antagonist.

c. Comparison of changes of the current before and after the administration of IV-12 showed that IV-12 had stronger suppression on NMDA peak current than on the steady-state current. The analysis of the receptor kinetics showed that IV-12 accelerated current desensitization as it depressed the peak current of NMDA. No obvious effect was seen using double pulse NMDA administration to restore desensitized NMDA receptors.

d. The antagonistic action of IV-12 membrane potential or the agonist independent, showing that it does not act on the internal $mg^{2+}$ site and the non-competitive antagonist site in the receptor channel. Changing the Gly concentration and pH value in external fluid, adding $Zn^{2+}$ and redox agent DTT did not change the $IC_{50}$ of IV-12. These results showed that IV-12 does not act on the Gly site, the $H^+$, $Zn^{2+}$ site or the redox site.

e. Spermine can decreased the inhibition intensity of IV-12 for NMDA receptor. 200 μM spermine shifted the inhibition curve induced by NMDA current sensing to the right, indicating that IV-12 acts on the polyamine site of the NMDA receptor.

(3) The binding test with NMDA receptor showed IV-12 (0.1 μM, 1 μM and 10 μM) has no antagonism on Glu site, Gly site and ion-channel site of the NMDA receptor.

3. The Action Type of IV-12

IV-12 had no defervescence effect (p.o., 60 mg/kg) on rats administrated with Brewers' yeast (s.c. 7%); it had no antagonism for swelling caused by p-dimethylbenzene after administration (p.o. 15 or 30 mg/kg) in mice. The Mice appeared quiet and suppressed from spontaneous activities after administration of IV-12 (p.o. 15 or 30 mg/kg).

The experiment results show that IV-12 hasn't the antithermic and anti-inflammatory effects, but does have an obvious inhibition effect on the control nervous system.

4. The Drug Dependence of IV-12

Physical drug dependence for IV-12 was evaluated with models of mouse jumping and rat precipitated withdrawal test. Psychological dependence was evaluated with models of mouse conditional position preference and the rat's drug discrimination. The results show that IV-12 has induced withdrawal syndrome in the precipated withdrawal model of but the effect is weaker than that of Morphine. In the spontaneous withdrawal model, the weight of the rats seems to increase rather than decrease, but there is no indication for withdrawal syndrome. IV-12 can cause an effect of position deviation in mice, but it displayed no discriminating effect in the discrimination test in rats.

In summary, the results showed that IV-12 itself does not generate physical dependence, its psychological dependence is quite low, and is only shown in sensitive test models. The details of experimental results are as follows:

(1) The Jumping Test in Mice

Sixty-four mice were divided into 4 groups (16 for each group, ♀♂fifty-fifty) Morphine, IV-12-1 (75 mg/Kg) IV-12-2 (100 mg/Kg) and saline were administrated respectively 3 times per day for 7 days with progressive dose increase. On the $7^{th}$ day, Narcan is injected (i.p. 2 mg/kg) to precipitate withdrawal. The number of times for the mice to jump was recorded and the incidence of the jump calculated. The results are in Table 7.

TABLE 7

| Group | Animal Number (n) | Times for jump (IV ± SD) | Incidence for jump (%) |
|---|---|---|---|
| Saline | 16 | 0 ± 0 | 0 |
| Morphine | 16 | 68 ± 43* | 87.5* |
| IV-12-1 | 16 | 9 ± 18# | 43.8*## |
| IV-12-2 | 16 | 33 ± 40*# | 62.5* |

*$P < 0.01$, compared with saline;
*#$P < 0.001$,
$P < 0.05$, compared with morphine (2) The Trial of Precipitated Withdrawal Test in Rats 48 rats were divided into 4 groups (12 for each group, ♀♂fifty-fifty). Morphines IV-12-1 (75 mg/Kg), IV-12-2 (100 mg/Kg) and saline, was administrated respectively using progressive dose increase for 14 days and 3 times per day. On the $15^{th}$ day, Narcan is injected (i.p. 4 mg/kg) to precipitate withdrawal. The withdrawal syndrome was observed and the rats wre weighed at 30, 60 and 120 minutes after the injection respectively. The results are in Table 8.

TABLE 8

| | | Abstinence syndrome | Percent of the lost weight (IV ± SD) | | |
|---|---|---|---|---|---|
| Group | Animal number (IV ± SD) | | 30 min | 60 min | 120 min |
| Saline | 12 | 0.0 ± 0.0* | −0.7 ± 1.6 | −1.0 ± 0.3 | −1.5 ± 0.6 |
| Morphine | 12 | 9.2 ± 2.8* | −5.1 ± 0.7* | −5.9 ± 1.0* | −7.0 ± 0.7* |

TABLE 8-continued

| Group | Abstinence syndrome Animal number (IV ± SD) | Percent of the lost weight (IV ± SD) | | |
|---|---|---|---|---|
| | | 30 min | 60 min | 120 min |
| IV-12-1 | 12 | 4.7 ± 3.9*# | −1.8 ± 1.4**# | −2.6 ± 1.5*# | −3.1 ± 1.5*# |
| IV-12-2 | 12 | 5.3 ± 2.1*# | −3.1 ± 1.3*# | −3.9 ± 1.4*# | −4.2 ± 1.5*# |

*$P < 0.01$,
**$P < 0.05$, compared with saline;
$P < 0.01$, compared with Morphine (3) Spontaneous Withdrawal Tests 96 mice were divided into 4 groups (24 for each group, ♀♂fifty-fifty), and Morphine, IV-12-1, IV-12-2, warm boiled water were administered respectively, using progressive dose increase for 7 days (i.g.) and 2 times per day. The weight of the rats after drug withdrawal was compared with the weight one day before drug withdrawal at a corresponding time (See Table 9 and 10).

of the rat in the group of IV-12-1, IV-12-2 and the group of warm boiled water did not decrease. On the contrary, their weight appeared to increase and there was no indication of withdrawal syndrome.

(4) Conditional Position Preference Test in Mice 30 mice were divided into 3 groups (10 for each group, ♀♂fifty-fifty): IV-12-1 (1 mg/kg), IV-12-2 (5 mg/kg) and NS. Half of the mice in each group were administrated (s.c.) in

TABLE 9

| Group | Sex | Different time after withdrawal (h) | | | | | | |
|---|---|---|---|---|---|---|---|---|
| | | 18 | 42 | 66 | 90 | 114 | 138 | 162 |
| Morphine | ♂ | 0.97 ± 0.04 | 0.91 ± 0.03 | 0.90 ± 0.03 | 0.94 ± 0.03 | 0.97 ± 0.03 | 0.99 ± 0.04 | 1.01 ± 0.04 |
| | ♀ | 0.98 ± 0.03 | 0.92 ± 0.02 | 0.91 ± 0.02 | 0.94 ± 0.02 | 0.97 ± 0.03 | 1.00 ± 0.03 | 1.01 ± 0.03 |
| IV-12-1 | ♂ | 1.01 ± 0.03 | 1.02 ± 0.03 | 1.04 ± 0.04 | 1.06 ± 0.05 | 1.08 ± 0.05 | 1.11 ± 0.06 | 1.12 ± 0.09 |
| 75 mg/kg | ♀ | 1.01 ± 0.03 | 1.02 ± 0.05 | 1.03 ± 0.04 | 1.04 ± 0.06 | 1.06 ± 0.06 | 1.08 ± 0.06 | 1.08 ± 0.07 |
| IV-12-2 | ♂ | 0.99 ± 0.04 | 1.00 ± 0.04 | 1.00 ± 0.05 | 1.00 ± 0.04 | 1.01 ± 0.04 | 1.03 ± 0.06 | 1.04 ± 0.08 |
| 100 mg/kg | ♀ | 1.01 ± 0.04 | 1.01 ± 0.05 | 1.01 ± 0.06 | 1.02 ± 0.06 | 1.02 ± 0.07 | 1.04 ± 0.07 | 1.04 ± 0.07 |

TABLE 10

| | | Morphine | | IV-12-1 (75 mg/kg) | | IV-12-2 (75 mg/kg) | | Warm boiled water | |
|---|---|---|---|---|---|---|---|---|---|
| | | Weight (g) | Increase (%) | Weight (g) | Increase (%) | Weight (g) | Increase (%) | Weight (g) | Increase (%) |
| Different time after withdrawal (h) | Before withdraw | 286.2 ± 40 | | 241.1 ± 38 | | 254.8 ± 32 | | 260.7 ± 33 | |
| | 12 | 284.7 ± 40 | −0.5 | 248.1 ± 42 | 2.9 | 259.8 ± 34 | 2.0 | 264.3 ± 37 | 1.4 |
| | 18 | 276.9 ± 39 | −3.2 | 250.5 ± 39 | 3.9 | 259.8 ± 33 | 2.0 | 261.3 ± 35 | 0.2 |
| | 24 | 267.9 ± 37 | −6.4 | 246.3 ± 37 | 2.2 | 255.9 ± 32 | 0.4 | 263.2 ± 33 | 1.0 |
| | 36 | 262.7 ± 37 | −8.2 | 253.9 ± 38 | 5.3 | 259.5 ± 33 | 1.9 | 270.6 ± 36 | 3.8 |
| | 42 | 258.4 ± 35 | −9.7 | 251.3 ± 37 | 4.3 | 258.5 ± 32 | 1.4 | 264.3 ± 34 | 1.4 |
| | 48 | 257.0 ± 33 | −10.2 | 249.1 ± 36 | 3.3 | 256.8 ± 31 | 0.8 | 265.0 ± 34 | 1.7 |
| | 60 | 256.6 ± 31 | −10.3 | 258.5 ± 38 | 7.2 | 259.6 ± 31 | 1.9 | 268.3 ± 30 | 2.9 |
| | 66 | 256.0 ± 34 | −10.5 | 252.8 ± 37 | 4.8 | 256.8 ± 27 | 0.8 | 264.6 ± 31 | 1.5 |
| | 72 | 260.4 ± 36 | −9.0 | 251.6 ± 36 | 4.4 | 255.7 ± 29 | 0.4 | 265.6 ± 34 | 1.9 |
| | 84 | 268.7 ± 37 | −6.1 | 263.7 ± 40 | 9.4 | 263.6 ± 30 | 3.4 | 272.5 ± 37 | 4.5 |
| | 90 | 264.7 ± 37 | −7.5 | 257.4 ± 39 | 6.8 | 258.2 ± 30 | 1.3 | 267.4 ± 36 | 2.6 |
| | 96 | 269.0 ± 40 | −6.0 | 254.2 ± 43 | 5.4 | 257.1 ± 28 | 0.9 | 267.2 ± 36 | 2.5 |
| | 108 | 277.6 ± 38 | −3.0 | 268.6 ± 42 | 11.4 | 266.3 ± 33 | 4.5 | 274.1 ± 39 | 5.1 |
| | 114 | 272.9 ± 38 | −4.7 | 261.6 ± 40 | 8.5 | 260.1 ± 30 | 2.1 | 268.8 ± 38 | 3.1 |
| | 120 | 275.4 ± 40 | −3.8 | 260.3 ± 40 | 8.0 | 258.3 ± 29 | 1.4 | 270.1 ± 39 | 3.6 |
| | 132 | 284.6 ± 38 | −0.5 | 275.8 ± 41 | 14.4 | 272.6 ± 35 | 7.0 | 273.9 ± 37 | 5.1 |
| | 138 | 279.3 ± 38 | −2.4 | 268.3 ± 41 | 11.3 | 264.9 ± 32 | 4.0 | 269.6 ± 37 | 3.4 |
| | 144 | 282.0 ± 41 | −1.5 | 264.7 ± 42 | 9.8 | 263.6 ± 32 | 3.5 | 271.1 ± 39 | 4.0 |
| | 156 | 291.0 ± 40 | 1.7 | 279.0 ± 44 | 15.7 | 271.5 ± 40 | 6.6 | 279.5 ± 40 | 7.2 |
| | 162 | 284.2 ± 40 | −0.6 | 271.0 ± 44 | 12.4 | 267.2 ± 38 | 4.9 | 273.8 ± 39 | 5.0 |
| | 168 | 286.5 ± 42 | 0.1 | 269.2 ± 45 | 11.7 | 266.3 ± 36 | 4.5 | 272.9 ± 40 | 4.7 |

Tables 9 and 10 showed that after the drug withdrawal, the weight of the animals in the Morphine group decreased significantally, the greatest decrease was 10%. The recovery began 80-90 hours later. After 130-140 hours, the weight was similar to that of one day before withdrawal; The weight the morning and 30 minutes later put into a white box (with medicine), and trained for 30 minutes; Saline is administrated (s.c.) in the afternoon and 30 minutes later put into a black box (without medicine), and trained for 30 minutes. The other half of the group are given saline in the morning and IV-12 in the afternoon, other procedures are the same as above.

The two training periods were at least 6-hour apart and training was continuous for 6 days. On the 7$^{th}$ day, the staying time was tested in both of the boxes. The results are in Table 11.

TABLE 11

| Group | Animal Number | Staying time in box with medicine (s) |
| --- | --- | --- |
| NS | 10 | 428.9 ± 79.2 |
| IV-12 1 mg/kg | 10 | 496.4 ± 73.4* |
| IV-12 5 mg/kg | 10 | 452.8 ± 119.5 |

*P < 0.05, Compared with saline (5) The Trail of Conditional Position Preference in Rats A commercially available device for testing (Med Associates Inc.) was used. Measurements were automatically recorded by a computer.

The data are indicated by means of IV±SD, t-test was employed to compare the data in different groups. The rats were divided randomly into groups by weight, 12 for each group. They were positive control groups. Morphine groups, three dosages of IV-12 and the negative control group (SN). The experiments were divided into stages of accommodation, training and test. Accommodation: Open the doors between black box and grey box and the door between white box and grey box. put the rats in from the grey box; let them run free in the training box for 15 minutes for 4 days. Training: The white box is with medicine while the black one is without it. The period training is 10 days, the first day with the medicine while the second day not; the third day with the medicine while the fourth day not, so on and so forth. When carrying out the training with medicine, 15 minutes after the rat is administrated (i.g.) with medicine, it is put into the white box for 30 minutes. When the training is without medicine, 15 minutes after the rat is administrated (i.g.) with saline, it is put into the black box for 30 minutes. Test: On the 11$^{th}$ day, the rat is put into the training box, with the door open. The time the rat stays in each box, and the number of time it enters during 15 minutes were determined, and the percentage of the time staying in the white box to the time together in white box and black box is calculated (Table 12).

TABLE 12

| Group | Animal Number | Percent in the medicine box (%) |
| --- | --- | --- |
| Control group | 10 | 48.8 ± 10.3 |
| Morphine | 8 | 62.0 ± 8.0* |
| IV-12 10 mg/kg | 10 | 46.1 ± 16.3 |
| IV-12 20 mg/kg | 10 | 51.9 ± 9.8 |
| IV-12 50 mg/kg | 9 | 62.9 ± 5.4* |

*P < 0.01, Compared with the control group (6) Drug Discrimination Experiment in Rats The experiment of rat's drug discrimination is carried out with an automatic control system manufactured by the Chinese institute of Drug Dependence. The method of metabolite reinforcement is used to train the rats by the program of fixed rate (FR 10). IV-12 (0.1 mg/kg, 1.0 mg/kg) is used to carry out the test of drug discrimination. FR1 indicates that no stable discriminating behavior was formed after 6 weeks' discriminating training. The 8 rats in the Morphine group (4 mg/kg) form of resistant discriminating behaviors after 5 weeks' training (FR 10). IV-12 (0.1 mg/kg, 1.0 mg/kg) is based on rats that have formed resistant discriminating behaviors. The results showed that neither of the two dosages can substitute the rats that have formed the discriminating behaviors caused by morphine. It indicates that within the dosage and time in this experiment, IV-12 does not have obvious discriminating effect.

5. Acute Toxicity $LD_{50}$ (p.o.) is 309 mg/kg in mice and 414 mg/kg in rats, as determined with the Bliss method.

6. Bacterial Reverse-Mutation Assay (Ames TS) of IV-12

Strains: S. typhimurium $TA_{97}$, $TA_{98}$, $TA_{100}$ and $TA_{102}$

Results: The assay included two parts without $S_9$ and with $S_9$. In the system without $S_9$ $TA_{98}$ 5000 μg/plate, and with $S_9$ $TA_{97}$ 5000 μg/palte inhibitory effect on bacterial for the growth were seen. All other doses showed no inhibitory effect, and for all other strains bacterium. For all tested doses, there was no significant increase of revertants. Ames test for of IV-12 is negative.

The results mentioned above indicate that IV-12 has an apparent analgesic effect, which is quite similar to Morphine, but much more powerful than Paracetamol; IV-12 does not have the ability to reduce fever or inflammation, but it has a remarkable inhibition effect on central nervous system; IV-12 has no apparent affinity with the μ-receptor, and expresses an intensive inhibition to NMDA receptor, which indicates that it can be a new central non-addictive anodyne; the potential drug dependence of IV-12 is low and it also shows good oral absorption, significant therapeutic index and its Ames test result is negative.

We claim:

1. A compound of formula I:

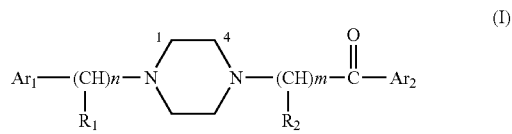

(I)

wherein $Ar_1$ and $Ar_2$ independently represent:

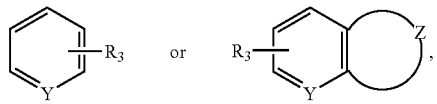

each of $R_1$, $R_2$ and $R_3$ represents any one of hydrogen, a $C_1$-$C_3$ alkyl group, a $C_5$ or $C_6$ cycloalkyl group, phenyl, substituted phenyl, hydroxyl, methoxy, ethoxy, amino, substituted amino, halogen, carboxylic acid, carboxylic ester, nitryl or acetonitrile group;

Y represents one of C, N, or O;

Z represents a five or six-membered ring containing carbon and optionally one of N or O.

2. The compound of claim 1, in the form of a racemate, enantiomer, diastereomer, a mixture of the enantiomers or diastereomers thereof.

3. The compound of claim 1, in the form of a physiologically compatible acidic and basic salt, a salt with a cation or a base or with anions and/or acids or in the form of a free acid or base.

4. The compound of claim 3, wherein the salt is selected from the group consisting of a hydrochloride, hydrobromide, sulfate, trifluoroacetate and methanesulfonate.

5. The compound according to claim 2, wherein the salt is hydrochloride or hydrobromide.

6. The compound according to claim 3, wherein, wherein the salt contains about 0.5-3 molecules of hydrate water.

7. The compound according to claim 3, wherein each of $R_1$, $R_2$ and $R_3$ represents any one of hydrogen, a $C_1$-$C_3$ alkyl, hydroxyl, methoxy, ethoxy, amino, substituted amino, halogen or nitryl group.

8. The compound according to claim 3, selected from the group consisting of:

IV-1 $N^1$-benzyl-$N^4$-phenacyl piperazine,
IV-2 $N^1$-(4-chlorobenzyl)-$N^4$-(1-benzoylethyl)piperazine,
IV-3 $N^1$-(4-chlorobenzyl)-$N^4$-phenacyl piperazine,
IV-4 $N^1$-(4-nitrobenzyl)-$N^4$-phenacyl piperazine,
IV-5 $N^1$-[(1-ethoxy-oxo-methyl)benzyl]-$N^4$-phenacyl piperazine,
IV-6 $N^1$-benzyl-$N^4$-(4-chlorophenacyl)piperazine,
IV-7 $N^1$-benzyl-$N^4$-(2-naphthoylmethyl)piperazine,
IV-8 $N^1$-benzyl-$N^4$-(4-methoxy phenacyl)piperazine,
IV-9 $N^1$-benzyl-$N^4$-(4-nitrophenacyl)piperazine,
IV-10 $N^1$-(4-methoxybenzyl)-$N^4$-phenacyl piperazine,
IV-11 $N^1$-(3-pyridylmethyl)-$N^4$-phenacyl piperazine,
IV-12 $N^1$-(4-aminobenzyl)-$N^4$-phenacyl piperazine,
IV-13 $N^1$-(4-aminobenzyl)-$N^4$-(1-benzoylethyl)piperazine,
IV-14 $N^1$-phenethyl-$N^4$-phenacyl piperazine,
IV-15 $N^1$-(2,5-dimethoxybenzyl)-$N^4$-phenacyl piperazine,
IV-16 $N^1$-benzyl-$N^4$-(4-aminophenacyl)piperazine,
IV-17 $N^1$-benzyl-$N^4$-(2-benzoylethyl)piperazine,
IV-18 $N^1$-(4-nitrobenzyl)-$N^4$-[(4-acetamido)phenacyl]piperazine,
IV-19 $N^1$-(3,4-methylenedioxybenzyl)-$N^4$-phenacyl piperazine,
IV-20 $N^1$-(4-fluorobenzyl)-$N^4$-(4-chlorophenacyl)piperazine,
IV-21 $N^1$-(4-acetamidobenzyl)-$N^4$-phenacyl piperazine,
IV-22 $N^1$-(3-phenylpropyl-3-ol)-$N^4$-(4-methoxyphenacyl)piperazine,
IV-23 $N^1$-(2-methoxy-5-nitrobenzyl)-$N^4$-phenacyl piperazine,
IV-24 $N^1$-[1-(4-fluorophenyl)ethyl]-$N^4$-phenacyl piperazine,
IV-25 $N^1$-(3-methoxybenzyl)-$N^4$-phenacyl piperazine,
IV-26 $N^1$-[(2-benzenesulfonylmethyl)benzyl]-$N^4$-phenacyl piperazine,
IV-27 $N^1$-[1-(4-nitrophenyl)ethyl]-$N^4$-(4-methylphenacyl)piperazine,
IV-28 $N^1$-benzyl-$N^4$-(5-chloro-6-methoxy-2-naphthoylmethyl)piperazine,
IV-29 $N^1$-benzyl-$N^4$-[1-(5-chloro-6-methoxy-2-naphthoyl) ethyl]piperazine,
IV-30 $N^1$-(3,4-methylenedioxybenzyl)-$N^4$-[1-(5-chloro-6-methoxy-2-naphthoyl)ethyl]piperazine,
IV-31 $N^1$-(4-methoxybenzyl)-$N^4$-[1-(5-chloro-6-methoxy-2-naphthoyl)ethyl]piperazine,
IV-32 $N^1$-(4-nitrobenzyl)-$N^4$-[1-(5-chloro-6-methoxy-2-naphthoyl)ethyl]piperazine,
IV-33 $N^1$-(4-aminobenzyl)-$N^4$-[1-(5-chloro-6-methoxy-2-naphthoyl)ethyl]piperazine,
IV-34 $N^1$-(3,4,5-trimethoxybenzyl)-N4-[1-(5-chloro-6-methoxy-2-naphthoyl-2-naphthoyl)ethyl]piperazine,
IV-35 $N^1$-cinnamyl-$N^4$-[1-(5-chloro-6-methoxy-2-naphthoyl)ethyl]piperazine,
IV-36 $N^1$-(3-chlorobenzyl)-$N^4$-[1-(5-chloro-6-methoxy-2-naphthoyl)ethyl]piperazine,
IV-37 $N^1$-(1-phenylethyl)-$N^4$-phenacyl piperazine,
IV-38 $N^1$—(R-1-phenylethyl)-$N^4$-phenacyl piperazine,
IV-39 $N^1$-(S-1-phenylethyl)-$N^4$-phenacyl piperazine,
IV-40 $N^1$-(1-phenylethyl)-$N^4$-(4-methylphenacyl)piperazine,
IV-41 $N^1$—(R-1-phenylethyl)-$N^4$-(4-methylphenacyl)piperazine,
IV-42 $N^1$-(S-1-phenylethyl)-$N^4$-(4-methylphenacyl)piperazine,
IV-43 $N^1$-(1-phenylethyl)-$N^4$-[1-(5-chloro-6-methoxy-2-naphthoyl)ethyl]piperazine,
IV-44 $N^1$-(S-1-phenylethyl)-$N^4$-[1-(5-chloro-6-methoxy-2-naphthoyl)ethyl]piperazine,
IV-45 $N^1$—(R-1-phenylethyl)-$N^4$-[1-(5-chloro-6-methoxy-2-naphthoyl)ethyl]piperazine,
IV-46 $N^1$-(4-chlorobenzyl)-$N^4$-phenacyl piperazine,
IV-47 $N^1$-(4-nitrobenzyl)-$N^4$-(1-benzoylethyl)piperazine,
IV-48 $N^1$-(1-phenylethyl)-$N^4$-(1-benzoylethyl)piperazine,
IV-49 $N^1$-(2,4-dichlorobenzyl)-$N^4$-phenacyl piperazine,
IV-50 $N^1$-(4-chlorobenzyl)-$N^4$-(4-chlorophenacyl)piperazine,
IV-51 $N^1$-[(1-hydroxy-oxo-methyl)benzyl]-$N^4$-phenacyl piperazine,
IV-52 $N^1$-[(1-ethoxy-oxo-methyl) benzyl]-$N^4$-(1-benzoylethyl)piperazine,
IV-53 $N^1$-(4-fluorobenzyl)-$N^4$-phenacyl piperazine,
IV-54 $N^1$-benzyl-$N^4$-[2-(benzylamino)-2-oxo-ethyl]piperazine,
IV-55 $N^1$-benzyl-$N^4$-(4-acetamido phenacyl)piperazine,
IV-56 $N^1$-benzyl-$N^4$-[1-oxo-2-(4-phenylpiperazin-1-yl) ethyl]piperazine,
IV-57 $N^1$-benzyl-$N^4$-(1-benzoylbenzyl)piperazine,
IV-58 $N^1$-(1-naphthalenylmethyl)-$N^4$-phenacyl piperazine,
IV-59 $N^1$-(2-naphthalenylmethyl)-$N^4$-phenacyl piperazine,
IV-60 $N^1$-[1-(4-nitrophenyl)ethyl]-$N^4$-phenacyl piperazine,
IV-61 $N^1$-(1-phenylpropyl)-$N^4$-phenacyl piperazine,
IV-62 $N^1$-(4-nitrobenzyl)-$N^4$-[2-(benzylamino)-2-oxoethyl]piperazine,
IV-63 $N^1$-(4-benzyloxybenzyl)-$N^4$-phenacyl piperazine, and
IV-64 $N^1$-(4-aminobenzyl)-$N^4$-[2-(benzylamino)-2-oxoethyl]piperazine.

9. The compound according to claim 8, wherein the compound is IV-12 $N^1$-(4-aminobenzyl)-$N^4$-phenacyl piperazine.

10. A pharmaceutical composition comprising a compound according to claim 3, and a pharmaceutically acceptable excipient.

11. A method for pain treatment, comprising administering to an animal in need thereof an effective pain-relieving amount of a pharmaceutical composition of claim 10 to the animal.

* * * * *